United States Patent
Srivastava

(10) Patent No.: US 11,066,676 B2
(45) Date of Patent: Jul. 20, 2021

(54) METHOD, VECTORS, CELLS, SEEDS AND KITS FOR STACKING GENES INTO A SINGLE GENOMIC SITE

(71) Applicant: THE BOARD OF TRUSTEES OF THE UNIVERSITY OF ARKANSAS, Little Rock, AR (US)

(72) Inventor: Vibha Srivastava, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 16/290,573

(22) Filed: Mar. 1, 2019

(65) Prior Publication Data

US 2019/0323021 A1 Oct. 24, 2019

Related U.S. Application Data

(62) Division of application No. 15/114,724, filed as application No. PCT/US2015/013845 on Jan. 30, 2015, now Pat. No. 10,233,456.

(60) Provisional application No. 61/933,646, filed on Jan. 30, 2014.

(51) Int. Cl.
C12N 15/82 (2006.01)
(52) U.S. Cl.
CPC ................ *C12N 15/8213* (2013.01)
(58) Field of Classification Search
None
See application file for complete search history.

(56) References Cited

U.S. PATENT DOCUMENTS

| 6,753,460 B2 * | 6/2004 | Fabijanski | C12N 15/8216 800/260 |
| 8,034,994 B2 | 10/2011 | Song et al. | |
| 8,329,986 B2 | 12/2012 | Butler et al. | |
| 8,450,471 B2 * | 5/2013 | Voytas | C12N 15/102 536/23.4 |
| 2005/0054106 A1 | 3/2005 | Ow et al. | |
| 2009/0191597 A1 | 7/2009 | Samulski et al. | |
| 2010/0162428 A1 | 6/2010 | Brown et al. | |

(Continued)

FOREIGN PATENT DOCUMENTS

WO  WO 2007011733  1/2007

OTHER PUBLICATIONS

Weide et al. A recombinase system facilitates cloning of expression cassettes in the ciliate Tetrahymena thermophila. (2007) BMC Microbiology; vol. 7 pp. 1-11 (Year: 2007).*

(Continued)

*Primary Examiner* — Cathy Kingdon Worley
(74) *Attorney, Agent, or Firm* — Quarles & Brady LLP

(57) ABSTRACT

Methods of gene stacking are described herein. The methods can be used to repeatedly add genes into a chosen locus in a precise manner, which ensures co-segregation of all introduced genes and contributes to the stabilization of gene expression. In addition, methods of removing any additional foreign DNA elements such as selectable markers are provided. Seed stocks or cell lines comprising a gene stacking site, vectors containing an insert flanked by target sites for a site-specific DNA recombinase for use in the methods and kits for carrying out the methods are also provided herein.

4 Claims, 15 Drawing Sheets

Specification includes a Sequence Listing.

pNS27

(56) References Cited

U.S. PATENT DOCUMENTS

| | | |
|---|---|---|
| 2011/0165679 A1 | 7/2011 | Gordon-Kamm et al. |
| 2011/0287545 A1 | 11/2011 | Cost et al. |
| 2012/0214228 A1* | 8/2012 | Voytas .................. C12N 15/62 435/320.1 |

OTHER PUBLICATIONS

Wang et al. Recombinase technologies: applications and possibilities. (2011) Plant Cell Rep; vol. 30; pp. 267-285 (Year: 2011).*

Aryan et al. Germline excision of transgenes in Aedes aegypti by homing endonucleases. (2013) Scientific Reports; vol. 3; pp. 1-8 (Year: 2013).*

Albert, H. et al. (1995) Site-specific integration of DNA into wild-type and mutant lox sites placed in the plant genome. Plant J. 7:649-59.

Antunes, M.S., et al. Targeted DNA excision in *Arabidopsis* by a re-engineered homing endonuclease. BMC Biotechnology. 2012. 12:86.

Aryan, A., et al. Germline excision of transgenes in Adedes aegypti by homing endonucleases. (2013) Scientific Reports; (3):1-8.

Chawla, R. et al. Transgene expression produced by biolistic-mediated, site-specific gene integration is consistently inherited by the subsequent generations. (2006) Plant Biotech J. 4: 209-218.

D'Halluin, K., et al. Homologous recombination: a basis for targeted genome optimization in crop species such as maize. (2008) Plant Biotech. J. 6:93-102.

De Pater, S., et al. ZFN-mediated gene targeting of the *Arabidopsis* protoporphyrinogen oxidase gene through Agrobacterium-mediated floral dip transformation. (2012) Plant Biotech. J. doi: 10.1111/pbi.12040.

Dietz-Pfeilstetter, A. Stability of transgene expression as a challenge for genetic engineering. (2010) Plant Science 179:164-7.

Fauser, F., et al. In planta gene targeting. (2012) Proc. Natl. Acad. Sci. USA 109:7535-40.

Gao, H. et al. Heritable targeted mutagenesis in maize using a designed endonuclease. (2010) Plant J. 61:176-87.

Halpin, C. Gene stacking in transgenic plants—the challenge for 21st century plant biotechnology. (2005) Plant Biotech. J. 3:141-55.

Kapusi, E., et al. phiC31 integrase-mediated site-specific recombination in barley. (2012) PLoS One 7:e45353.

Kempe, K., et al. Transgene excision from wheat chromosomes by phage phiC31 integrase. (2010) Plant Mol Biol. 72:673-87.

Li, Z., et al. Site-specific integration of transgenes in soybean via recombinase-mediated DNA cassette exchange. (2009) Plant Physiol., 151: 1087-1095.

Li, Z. et al. Stacking multiple transgenes at a selected genomic site via repeated recombinase-mediated DNA cassette exchanges. Plant Physiology. 2010. vol. 154. pp. 622-631.

Lloyd, A.H., et al. Single molecule PCR reveals similar patterns of non-homologous DSB repair in tobacco and *Arabidopsis*. School of Molecular and Biomedical Science. 2012. vol. 7:2.

Lutz, K.A., et al. A novel approach to plastid transformation utilizes the phiC31 phage integrase. (2004) Plant J. 37:906-13.

Nandy, S. & Srivastava, V. Site-specific gene integration in rice genome mediated by the FLP-FRT recombination system. Plant Biotechnology Journal. 2010. pp. 1-11.

Nandy, S. & Srivastava, V. Marker-free site-specific gene integration in rice based on the use of two recombination systems. (2012) Plant Biotech. J. 10: 904-912.

Nanto, K. et al. Expression of a transgene exchanged by the recombinase-mediated cassette exchange (RMCE) method in plants. (2009) Plant Cell Rep. 28:777-85.

Ow, D.W. Recombinase-mediated gene stacking as a transformation operating system. J. Integr. (2011) Plant Biol. 53:512-9.

Perez, E. et al. Establishment of HIV-1 resistance in CD4+ T cells by genome editing using zinc-finger nucleases. 2008. Nat Biotechnol. 26, 808-816.

Petolino, J.F., et al. Zinc finger nuclease-mediated transgene deletion. (2010) Plant Mol. Biol. 73:617-628.

Puchta, H. The repair of double-strand breaks in plants: mechanisms and consequences for genome evolution. (2005) J. Exp. Bot. 56: 1-14.

Que, Q., et al. Trait stacking in transgenic crops: Challenges and opportunities. (2010) GM Crops 1:4, 220-229.

Rosellini, D. et al. Selectable markers and reporter genes: a well furnished toolbox for plant science and genetic engineering. 2012. Critical Reviews in Plant Sciences. 31:401-453.

Rubtsova, M., et al. Expression of active Streptomyces phage phiC31 integrase in transgenic wheat plants. (2008) Plant Cell Rep. 27:1821-31.

Shukla, V.K., et al. Precise genome modification in the crop species *Zea mays* using zinc-finger nucleases (2009) Nature 459: 437-441.

Srivastava, V. et al. Cre-mediated site-specific gene integration for consistent transgene expression in rice. Plant Biotechnology Journal. 2004. vol. 2, 169-179.

Srivastava, V. & Ow, D.W. Biolistic Mediated site-specific integration in rice. (2002) Mol. Breed. 8: 345-350.

Srivastava, V. & Ow, D.W. Marker-free site-specific gene integration in plants. (2004) Trends Biotech. 12: 627-630.

Srivastava, V. & Thomson. Gene stacking by recombinases. Review Article. Plant Biotechnology Journal. 2016. vol. 14. 471-482.

Thomson, J.G., et al. PhiC31 recombination system demonstrates heritable germinal transmission of site-specific excision from the *Arabidopsis* genome. (2010) BMC Biotechnol. 10:17.

Townsend, J.A., et al. High-frequency modification of plant genes using engineered zinc-finger nucleases. (2009) Nature 459: 442-445.

Tzfira, T. et al. Genome modifications in plant cells by custom-made restriction enzymes. Plant Biotechnology Journal. 2012. vol. 10. pp. 373-389.

Vergunst, A.C., et al. Site-specific integration of Agrobacterium T-DNA in *Arabidopsis thaliana* mediated by Cre recombinase. (1998) Nucleic Acids Res. 26:2729-34.

Wang, Y. et al., Recombinase technology: applications and possibilities. (2011) Plant Cell Rep; 930):267-285.

Weinthal, D. et al. Non-homologous end-joining-mediated gene replacement in plant cells. (2013) Plant Physiol. 162:390-400.

Zhang, Y., et al. Transcription activator-like effector nucleases enable efficient plant genome engineering. (2013) Plant Physiol. 161(1):20-7.

International Search Report and Written Opinion for PCT/US2015/013845 dated May 7, 2015.

Office Action for U.S. Appl. No. 15/114,724 dated Jan. 10, 2018 (19 pages).

* cited by examiner

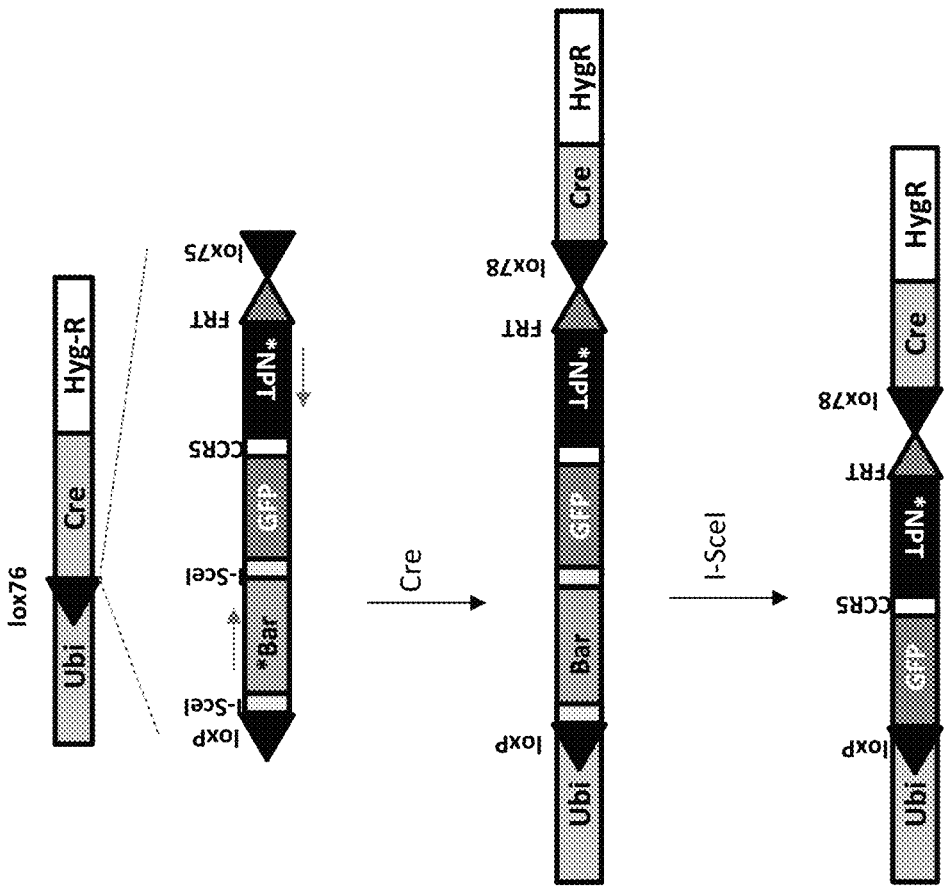
Figure 6A  T5 site
Figure 6B  pNS27
Figure 6C  SSI
Figure 6D  Marker-free SSI

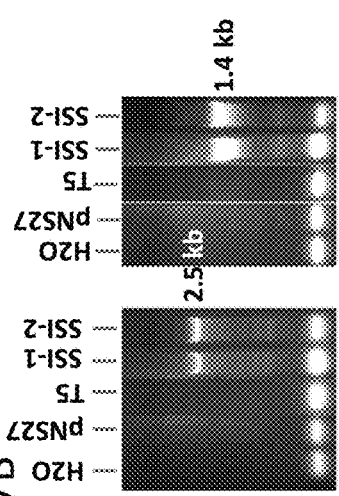
Figure 7A
T5-SSI structure
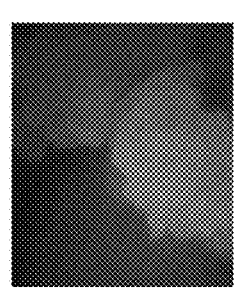
Figure 7B
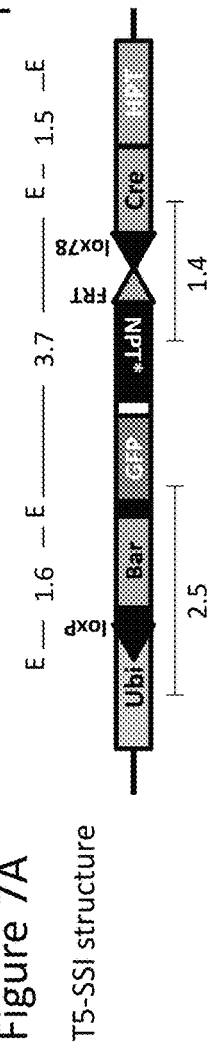
Figure 7C
Partial sequence of 2.5 kb amplicon (SEQ ID NO: 19)
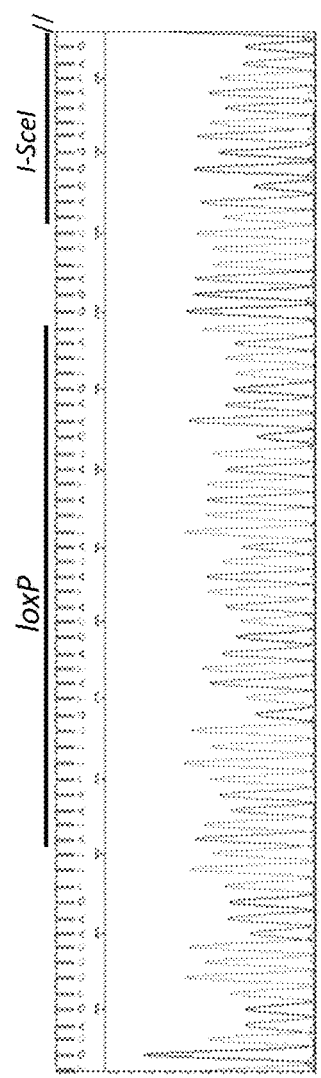
Figure 7D
Partial sequence of 1.4 kb amplicon (SEQ ID NO: 20)
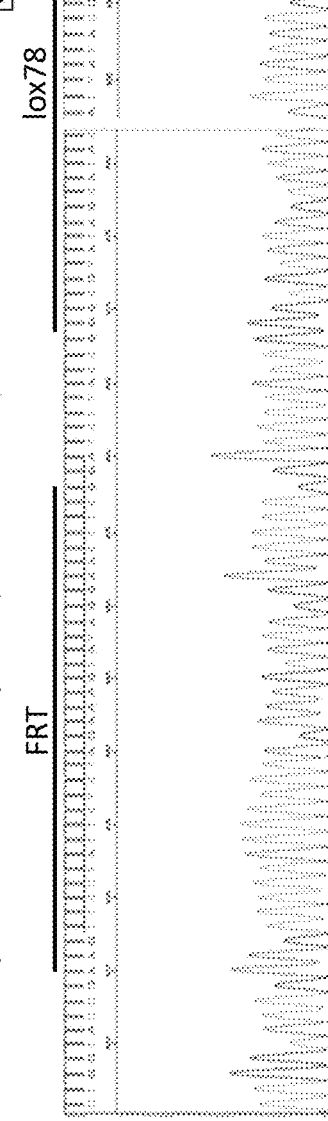
Figure 7E
Figure 7F

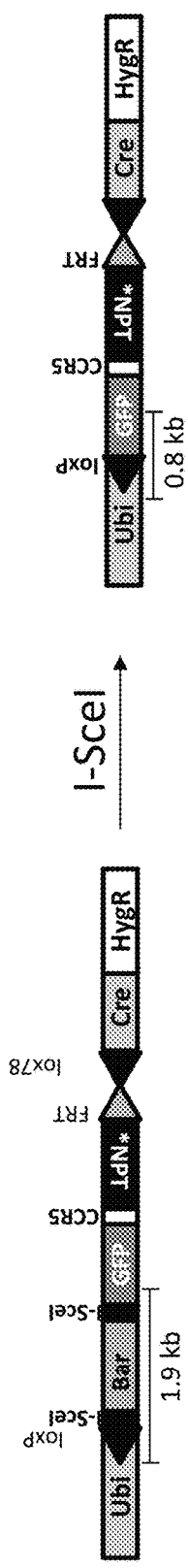
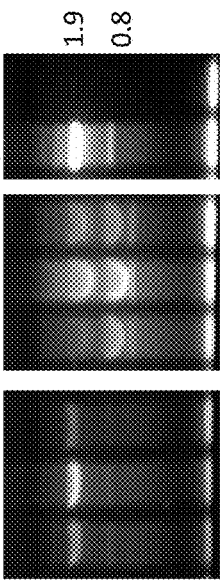
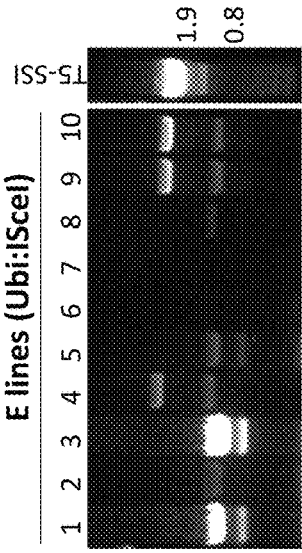
Figure 8A
Figure 8B
Figure 8C
Figure 8D
Figure 8E

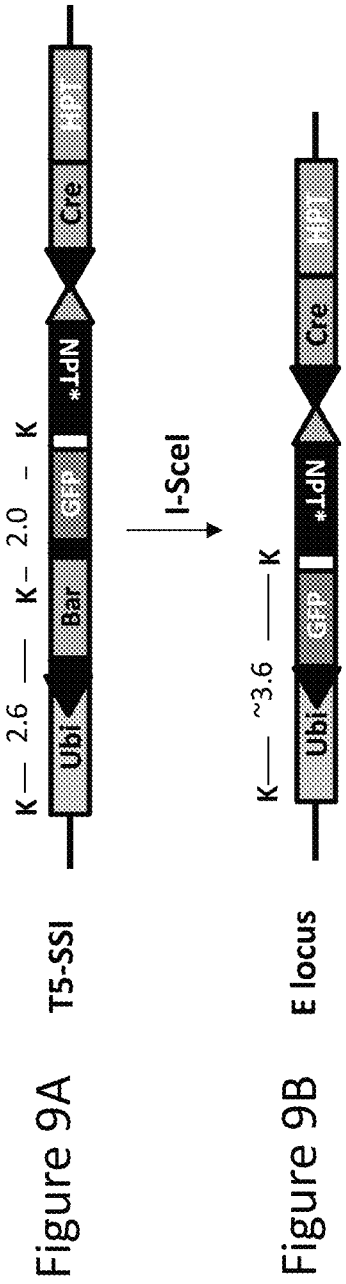
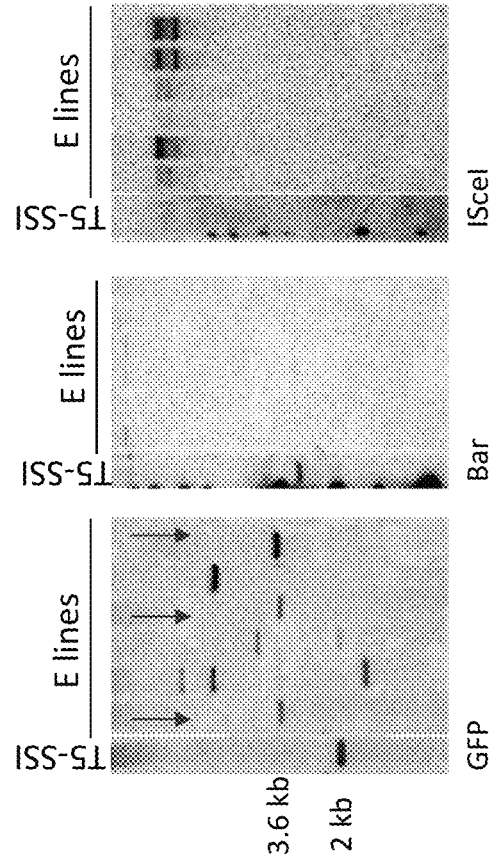
Figure 9A  Figure 9B  Figure 9C  Figure 9D  Figure 9E

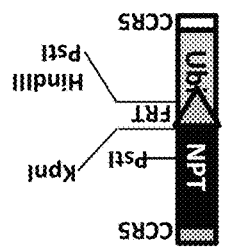

Figure 10F
SSI Structure

Figure 10A
Marker-free SSI (T5)

Figure 10B
pNS35

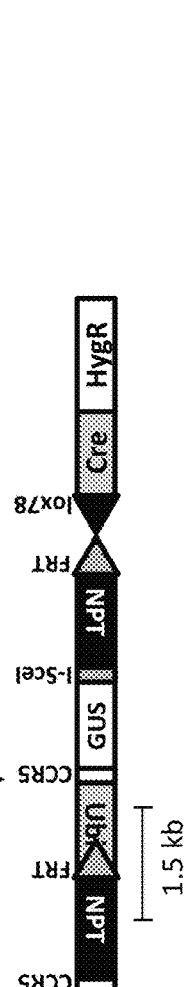

Figure 10C
Site-specific integration

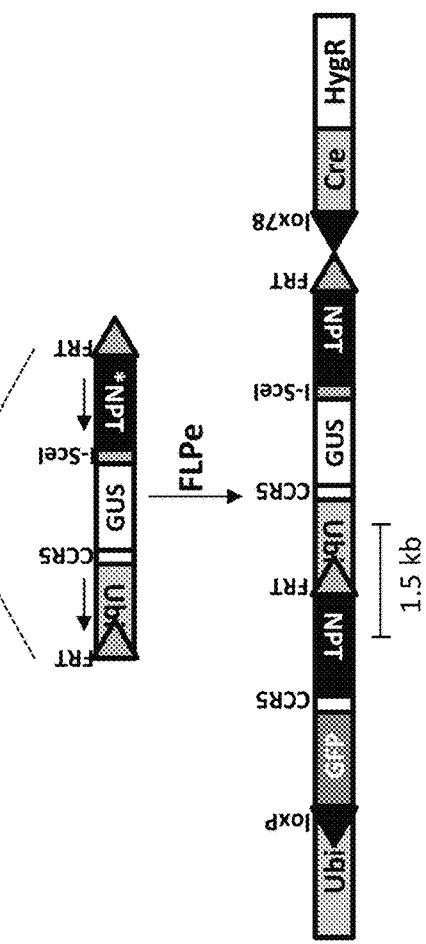

Figure 10D
PCR analysis

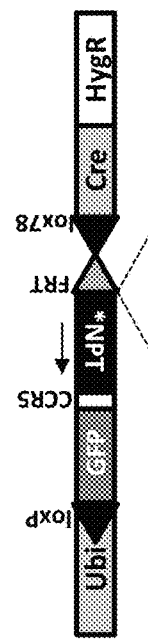

Figure 10E
SEQ ID NO: 24

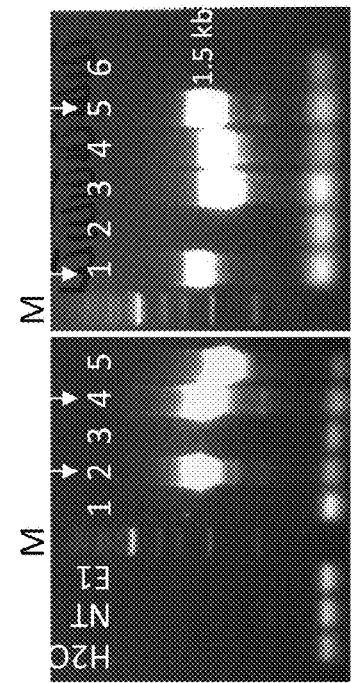

CTGCAGTTCATTCAGGGCACCGGACAGGTTGGTCTTGACAAA
AAGAACCGGGGCCCCTGCGCTGACAGCCGGAACACGGCGG
CATCAGAGCAGCCGATTGTCTGTTGTGCCCAGTCATAGCCGAA
TAGCCTCTCCACCCAAGCGCCGGAGAACTTGCGTGCAATCC
ATCTTGTTCAATCATGCGAAACGATCCTCTAGGATCGATCTGGT
ACGAAGTTCCTATTCTAGAAGTATAGGAACTTCGGATATG
TATGCTATACGAAGTTATAAGCTTGGGCGTGCAGAAGTAACACC
AAACAACAGGGTGAGCATCGACAAAGAAACAGTACCAAGCA
AATA

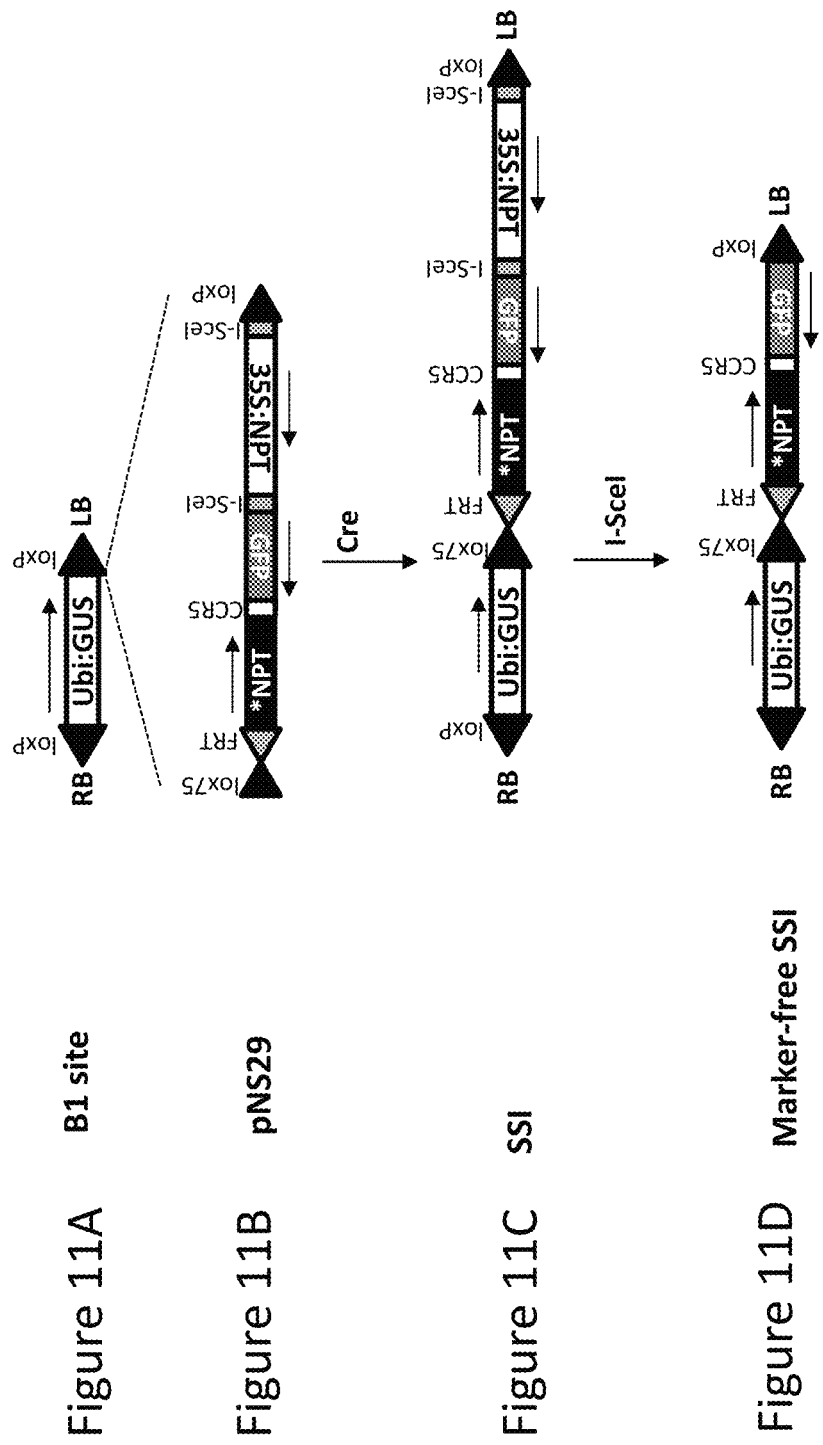
Figure 11A  B1 site
Figure 11B  pNS29
Figure 11C  SSI
Figure 11D  Marker-free SSI

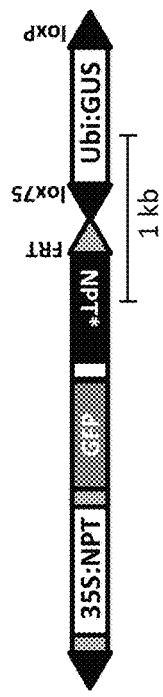
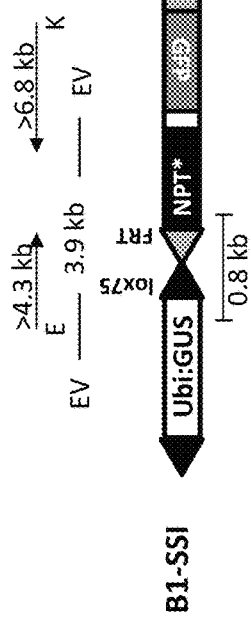
Figure 12A
Figure 12B
Figure 12C
Figure 12D
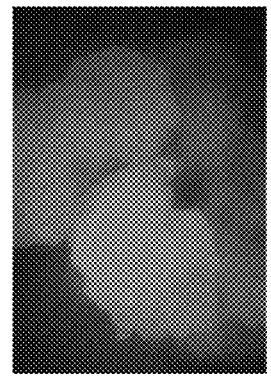
Figure 12E
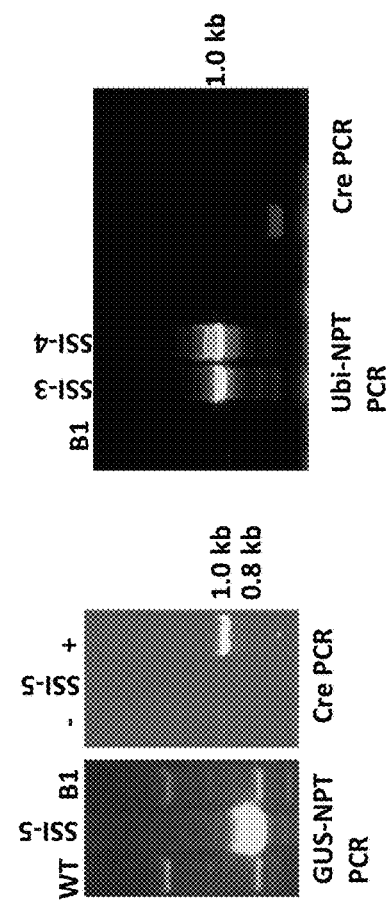
Figure 12G
Figure 12F Partial Sequence of 0.8 kb fragment from SSI-5 (SEQ ID NO: 25)
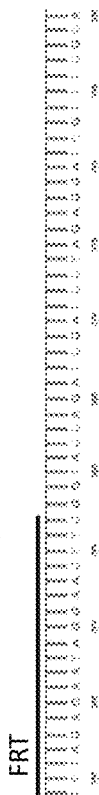
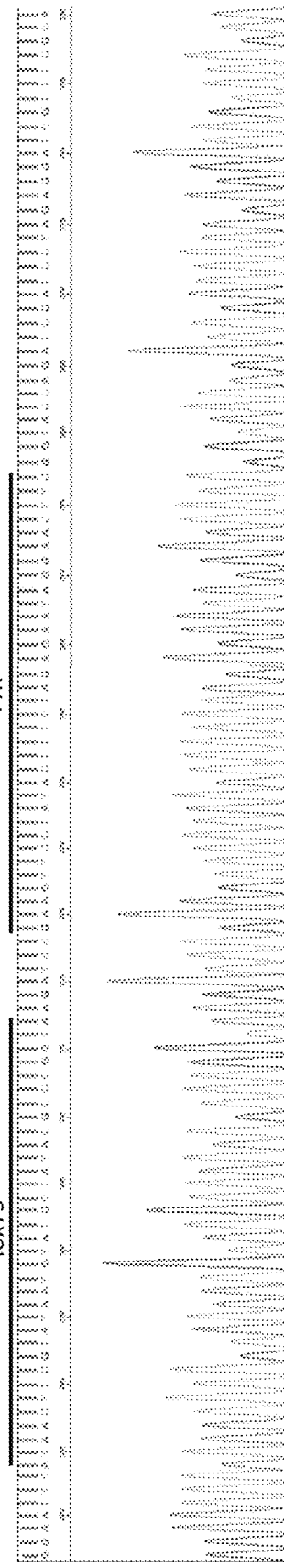

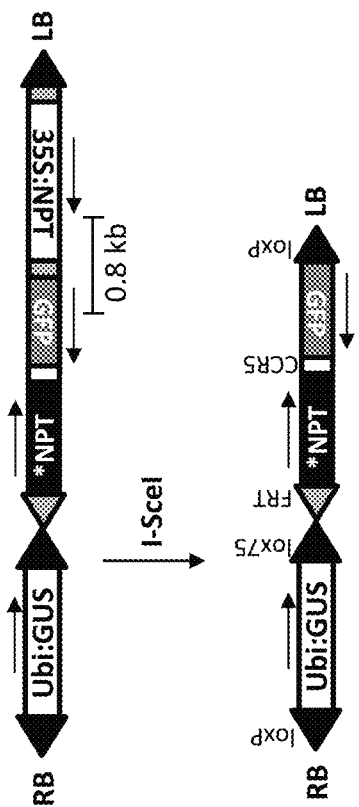
Figure 13A
B1-SSI
Figure 13B
Excision locus
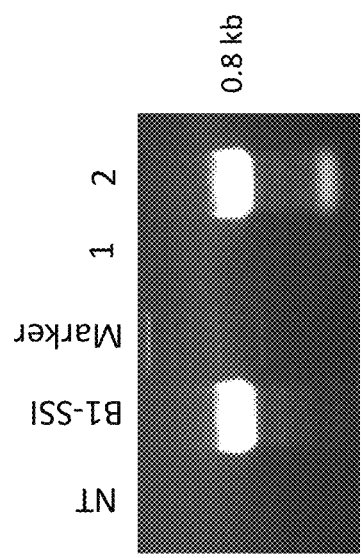
Figure 13C

SEQUENCE LISTING

```
<160> NUMBER OF SEQ ID NOS: 25

<210> SEQ ID NO 1
<211> LENGTH: 1032
<212> TYPE: DNA
<213> ORGANISM: Artificial Sequence
<220> FEATURE:
<223> OTHER INFORMATION: Synthetic: CRE recombinase polynucleotide

<400> SEQUENCE: 1
atgtccaatt tactgaccgt acaccaaaat ttgcctgcat taccggtcga tgcaacgagt      60
gatgaggttc gcaagaacct gatggacatg ttcagggatc gccaggcgtt ttctgagcat     120
acctggaaaa tgcttctgtc cgtttgccgg tcgtgggcgg catggtgcaa gttgaataac     180
cggaaatggt ttcccgcaga acctgaagat gttcgcgatt atcttctata tcttcaggcg     240
cgcggtctgg cagtaaaaac tatccagcaa catttgggcc agctaaacat gcttcatcgt     300
cggtccgggc tgccacgacc aagtgacagc aatgctgttt cactggttat gcggcggatc     360
cgaaaagaaa acgttgatgc cggtgaacgt gcaaaacagg ctctagcgtt cgaacgcact     420
gatttcgacc aggttcgttc actcatgaa aatagcgatc gctgccagga tatacgtaat     480
ctggcatttc tggggattgc ttataacacc ctgttacgta tagccgaaat tgccaggatc     540
agggttaaag atatctcacg tactgacggt gggagaatgt taatccatat tggcagaacg     600
aaaacgctgg ttagcaccgc aggtgtagag aaggcactta gcctgggggt aactaaactg     660
gtcgagcgat ggatttccgt ctctggtgta gctgatgatc cgaataacta cctgttttgc     720
cgggtcagaa aaaatggtgt tgccgcgcca tctgccacca gccagctatc aactcgcgcc     780
ctggaaggga tttttgaagc aactcatcga ttgatttacg gcgctaagga tgactctggt     840
cagagatacc tggcctggtc tggacacagt gcccgtgtcg gagccgcgcg agatatggcc     900
cgcgctggag tttcaataccc ggagatcatg caagctggtg gctggaccaa tgtaaatatt     960
gtcatgaact atatccgtaa cctggatagt gaaacagggg caatggtgcg cctgctggaa    1020
gatggcgatt ag                                                        1032

<210> SEQ ID NO 2
<211> LENGTH: 343
<212> TYPE: PRT
<213> ORGANISM: Artificial Sequence
<220> FEATURE:
<223> OTHER INFORMATION: Synthetic: Cre recombinase amino acid

<400> SEQUENCE: 2

Met Ser Asn Leu Leu Thr Val His Gln Asn Leu Pro Ala Leu Pro Val
```

```
            1               5                  10                 15
        Asp Ala Thr Ser Asp Glu Val Arg Lys Asn Leu Met Asp Met Phe Arg
                        20                  25                 30

Asp Arg Gln Ala Phe Ser Glu His Thr Trp Lys Met Leu Leu Ser Val
                        35                  40                 45

Cys Arg Ser Trp Ala Ala Trp Cys Lys Leu Asn Asn Arg Lys Trp Phe
                        50                  55                 60

Pro Ala Glu Pro Glu Asp Val Arg Asp Tyr Leu Leu Tyr Leu Gln Ala
         65                 70                  75                 80

Arg Gly Leu Ala Val Lys Thr Ile Gln Gln His Leu Gly Gln Leu Asn
                        85                  90                 95

Met Leu His Arg Arg Ser Gly Leu Pro Arg Pro Ser Asp Ser Asn Ala
                        100                 105                110

Val Ser Leu Val Met Arg Arg Ile Arg Lys Glu Asn Val Asp Ala Gly
                        115                 120                125

Glu Arg Ala Lys Gln Ala Leu Ala Phe Glu Arg Thr Asp Phe Asp Gln
                        130                 135                140

Val Arg Ser Leu Met Glu Asn Ser Asp Arg Cys Gln Asp Ile Arg Asn
         145                150                 155                160

Leu Ala Phe Leu Gly Ile Ala Tyr Asn Thr Leu Leu Arg Ile Ala Glu
                        165                 170                175

Ile Ala Arg Ile Arg Val Lys Asp Ile Ser Arg Thr Asp Gly Gly Arg
                        180                 185                190

Met Leu Ile His Ile Gly Arg Thr Lys Thr Leu Val Ser Thr Ala Gly
                        195                 200                205

Val Glu Lys Ala Leu Ser Leu Gly Val Thr Lys Leu Val Glu Arg Trp
                        210                 215                220

Ile Ser Val Ser Gly Val Ala Asp Pro Asn Asn Tyr Leu Phe Cys
         225                230                 235                240

Arg Val Arg Lys Asn Gly Val Ala Ala Pro Ser Ala Thr Ser Gln Leu
                        245                 250                255

Ser Thr Arg Ala Leu Glu Gly Ile Phe Glu Ala Thr His Arg Leu Ile
                        260                 265                270

Tyr Gly Ala Lys Asp Asp Ser Gly Gln Arg Tyr Leu Ala Trp Ser Gly
                        275                 280                285

His Ser Ala Arg Val Gly Ala Ala Arg Asp Met Ala Arg Ala Gly Val
                        290                 295                300

Ser Ile Pro Glu Ile Met Gln Ala Gly Gly Trp Thr Asn Val Asn Ile
         305                310                 315                320

Val Met Asn Tyr Ile Arg Asn Leu Asp Ser Glu Thr Gly Ala Met Val
                        325                 330                335

Arg Leu Leu Glu Asp Gly Asp
                        340

<210> SEQ ID NO 3
<211> LENGTH: 34
<212> TYPE: DNA
<213> ORGANISM: Artificial Sequence
<220> FEATURE:
<223> OTHER INFORMATION: Synthetic: loxP

<400> SEQUENCE: 3
ataacttcgt atagcataca ttatacgaag ttat                              34

<210> SEQ ID NO 4
```

```
<211> LENGTH: 34
<212> TYPE: DNA
<213> ORGANISM: Artificial Sequence
<220> FEATURE:
<223> OTHER INFORMATION: Synthetic: lox75

<400> SEQUENCE: 4
taccgggcgt atagcataca ttatacgaag ttat                           34

<210> SEQ ID NO 5
<211> LENGTH: 34
<212> TYPE: DNA
<213> ORGANISM: Artificial Sequence
<220> FEATURE:
<223> OTHER INFORMATION: Synthetic: lox76

<400> SEQUENCE: 5
ataacttcgt atagcataca ttatacgccc ggta                           34

<210> SEQ ID NO 6
<211> LENGTH: 34
<212> TYPE: DNA
<213> ORGANISM: Artificial Sequence
<220> FEATURE:
<223> OTHER INFORMATION: Synthetic: lox78

<400> SEQUENCE: 6
taccgggcgt atagcataca ttatacgccc ggta                           34

<210> SEQ ID NO 7
<211> LENGTH: 1272
<212> TYPE: DNA
<213> ORGANISM: Artificial Sequence
<220> FEATURE:
<223> OTHER INFORMATION: Synthetic: FLP recombinase polynucleotide

<400> SEQUENCE: 7
atgccacaat ttggtatatt atgtaaaaca ccacctaagg tgcttgttcg tcagtttgtg     60
gaaaggtttg aaagaccttc aggtgagaaa atagcattat gtgctgctga actaacctat   120
ttatgttgga tgattacaca taacggaaca gcaatcaaga gagccacatt catgagctat   180
aatactatca taagcaattc gctgagtttc gatattgtca taaaatcact ccagttaaaa   240
tacaagacgc aaaaagcaac aattctggaa gcctcattaa agaaattgat tcctgcttgg   300
gaatttacaa ttattcctta ctatggacaa aaacatcaat ctgatatcac tgatattgta   360
agtagtttgc aattacagtt cgaatcatcg gaagaagcag ataagggaaa tagccacagt   420
aaaaaaatgc ttaaagcact tctaagtgag ggtgaaagca tctgggagat cactgagaaa   480
atactaaatt cgtttgagta tacttcgaga tttacaaaaa caaaaacttt ataccaattc   540
ctcttcctag ctactttcat caattgtgga agattcagcg atattaagaa cgttgatccg   600
aaatcattta aattagtcca aaataagtat ctgggagtaa taatccagtg tttagtgaca   660
gagacaaaga caagcgttag taggcacata tacttcttta gcgcaagggg taggatcgat   720
ccacttgtat atttggatga attttttgagg aattctgaac cagtcctaaa acgagtaaat   780
aggaccggca attcttcaag caataaacag gaataccaat tattaaaaga taacttagtc   840
agatcgtaca ataaagcttt gaagaaaaat gcgccttatt caatctttgc tataaaaaat   900
ggcccaaaat ctcacattgg aagacatttg atgacctcat ttcttttcaat gaagggccta   960 acggagttga ctaatgttgt gggaaattgg agcgataagc gtgcttctgc cgtggccagg  1020
acaacgtata ctcatcagat aacagcaata cctgatcact acttcgcact agtttctcgg  1080
```

-continued

```
tactatgcat atgatccaat atcaaaggaa atgatagcat tgaaggatga gactaatcca    1140
attgaggagt ggcagcatat agaacagcta aagggtagtg ctgaaggaag catacgatac    1200
cccgcatgga atgggataat atcacaggag gtactagact acctttcatc ctacataaat    1260
agacgcatat aa                                                        1272

<210> SEQ ID NO 8
<211> LENGTH: 423
<212> TYPE: PRT
<213> ORGANISM: Artificial Sequence
<220> FEATURE:
<223> OTHER INFORMATION: Synthetic: amino acid of FLP

<400> SEQUENCE: 8

Met Pro Gln Phe Gly Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
                20                  25                  30

Leu Cys Ala Ala Glu Leu Thr Tyr Leu Cys Trp Met Ile Thr His Asn
            35                  40                  45

Gly Thr Ala Ile Lys Arg Ala Thr Phe Met Ser Tyr Asn Thr Ile Ile
        50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320
```

Thr Glu Leu Thr Asn Val Val Gly Asn Trp Ser Asp Lys Arg Ala Ser
            325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
            355                 360                 365

Lys Glu Met Ile Ala Leu Lys Asp Glu Thr Asn Pro Ile Glu Glu Trp
            370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
            405                 410                 415

Ser Tyr Ile Asn Arg Arg Ile
            420

<210> SEQ ID NO 9
<211> LENGTH: 1311
<212> TYPE: DNA
<213> ORGANISM: Artificial Sequence
<220> FEATURE:
<223> OTHER INFORMATION: Synthetic: FLPe (www.addgene.com; Plasmid
      #13787): polynucleotide

<400> SEQUENCE: 9

| | | | | | |
|---|---|---|---|---|---|
| atgagccaat | tgatatatt | atgtaaaaca | ccacctaagg | tcctggttcg | tcagtttgtg | 60 |
| gaaaggtttg | aaagaccttc | aggggaaaaa | atagcatcat | gtgctgctga | actaacctat | 120 |
| ttatgttgga | tgattactca | taacggaaca | gcaatcaaga | gagccacatt | catgagctat | 180 |
| aatactatca | taagcaattc | gctgagtttc | gatattgtca | caaatcact | ccagttaaa | 240 |
| tacaagacgc | aaaaagcaac | aattctggaa | gcctcattaa | agaattaat | tcctgcttgg | 300 |
| gaatttacaa | ttattcctta | caatggacaa | aaacatcaat | ctgatatcac | tgatattgta | 360 |
| agtagtttgc | aattacagtt | cgaatcatcg | gaagaagcag | ataagggaaa | tagccacagt | 420 |
| aaaaaaatgc | ttaaagcact | tctaagtgag | ggtgaaagca | tctgggagat | cactgagaaa | 480 |
| atactaaatt | cgtttgagta | tacctcgaga | tttacaaaaa | caaaaacttt | ataccaattc | 540 |
| ctcttcctag | ctactttcat | caattgtgga | agattcagcg | atattaagaa | cgttgatccg | 600 |
| aaatcattta | aattagtcca | aaataagtat | ctgggagtaa | taatccagtg | tttagtgaca | 660 |
| gagacaaaga | caagcgttag | taggcacata | tacttcttta | gcgcaagggg | taggatcgat | 720 |
| ccacttgtat | atttggatga | attttttgagg | aactctgaac | cagtcctaaa | acgagtaaat | 780 |
| aggaccggca | attcttcaag | caacaaacag | gaataccaat | tattaaaaga | taacttagtc | 840 |
| agatcgtaca | acaaggcttt | gaagaaaaat | gcgccttatc | caatctttgc | tataaagaat | 900 |
| ggcccaaaat | ctcacattgg | aagacatttg | atgacctcat | ttctgtcaat | gaagggccta | 960 |
| acggagttga | ctaatgttgt | gggaaattgg | agcgataagc | gtgcttctgc | cgtggccagg | 1020 |
| acaacgtata | ctcatcagat | aacagcaata | cctgatcact | acttcgcact | agtttctcgg | 1080 |
| tactatgcat | atgatccaat | atcaaaggaa | atgatagcat | tgaaggatga | gactaatcca | 1140 |
| attgaggagt | ggcagcatat | agaacagcta | aagggtagtg | ctgaaggaag | catacgatac | 1200 |
| cccgcatgga | atgggataat | atcacaggag | gtactagact | acctttcatc | ctacataaat | 1260 |
| agacgcatag | gaccggtgga | acaaaaactt | atttctgaag | aagatctgtg | a | 1311 |

<210> SEQ ID NO 10
<211> LENGTH: 427

```
<212> TYPE: PRT
<213> ORGANISM: Artificial Sequence
<220> FEATURE:
<223> OTHER INFORMATION: Synthetic: FLPe recombinase amino acid

<400> SEQUENCE: 10
```

| | | | | | | | | | | | | | | |
|---|---|---|---|---|---|---|---|---|---|---|---|---|---|---|
| Met | Ser | Gln | Phe | Asp | Ile | Leu | Cys | Lys | Thr | Pro | Pro | Lys | Val | Leu | Val |
| 1 | | | | 5 | | | | | 10 | | | | | 15 |

Arg Gln Phe Val Arg Phe Glu Arg Pro Ser Gly Glu Lys Ile Ala Ser
            20                  25                  30

Cys Ala Ala Glu Leu Thr Tyr Cys Trp Met Ile Thr His Asn Gly Thr
        35                  40                  45

Ala Ile Lys Arg Ala Thr Phe Met Ser Tyr Thr Ile Ile Ser Asn Ser
 50                  55                  60

Leu Ser Phe Asp Ile Val Asn Lys Ser Leu Gln Phe Lys Lys Thr Gln
65                  70                  75                  80

Lys Ala Thr Ile Leu Glu Ala Ser Leu Lys Lys Leu Ile Pro Ala Trp
                85                  90                  95

Phe Thr Ile Ile Pro Tyr Asn Gly Gln Lys His Gln Ser Asp Ile Thr
            100                 105                 110

Asp Ile Val Ser Ser Leu Gln Leu Gln Phe Glu Ser Ser Glu Glu Ala
            115                 120                 125

Asp Lys Gly Asn Ser His Ser Lys Met Leu Lys Ala Leu Leu Ser Glu
        130                 135                 140

Gly Glu Ser Ile Trp Glu Ile Thr Glu Lys Leu Asn Ser Phe Glu Tyr
145                 150                 155                 160

Thr Ser Arg Phe Thr Lys Thr Lys Thr Leu Tyr Gln Phe Phe Leu Ala
                165                 170                 175

Thr Phe Ile Asn Cys Gly Arg Phe Ser Asp Ile Lys Asn Val Asp Pro
            180                 185                 190

Lys Ser Phe Lys Leu Val Gln Asn Lys Tyr Leu Gly Val Ile Ile Gln
        195                 200                 205

Cys Leu Val Thr Thr Lys Thr Ser Val Ser Arg His Ile Tyr Phe Phe
210                 215                 220

Ser Ala Arg Gly Arg Ile Asp Pro Leu Val Tyr Leu Asp Glu Phe Leu
225                 230                 235                 240

Arg Asn Ser Glu Pro Val Leu Lys Arg Val Asn Arg Thr Gly Asn Ser
                245                 250                 255

Ser Ser Asn Lys Gln Glu Tyr Gln Leu Leu Lys Asp Asn Leu Val Arg
            260                 265                 270

Ser Tyr Asn Lys Ala Leu Lys Lys Asn Ala Pro Tyr Pro Ile Phe Ala
        275                 280                 285

Ile Lys Asn Gly Pro Lys Ser His Ile Gly Arg His Leu Met Thr Ser
290                 295                 300

Phe Leu Ser Met Lys Gly Leu Thr Glu Leu Thr Asn Val Val Gly Asn
305                 310                 315                 320

Trp Ser Asp Lys Arg Ala Ser Ala Val Ala Arg Thr Thr Tyr Thr His
                325                 330                 335

Gln Ile Thr Ala Ile Pro Asp His Tyr Phe Ala Leu Val Ser Arg Tyr
            340                 345                 350

Tyr Ala Tyr Asp Pro Ile Ser Lys Glu Met Ile Ala Leu Lys Asp Glu
        355                 360                 365

Thr Asn Pro Ile Glu Glu Trp Gln His Ile Glu Gln Leu Lys Gly Ser
370                 375                 380

```
Ala Glu Gly Ser Ile Arg Tyr Pro Ala Trp Asn Gly Ile Ile Ser Gln
385                 390                 395                 400

Glu Val Leu Asp Tyr Leu Ser Ser Tyr Ile Asn Arg Arg Ile Gly Pro
                405                 410                 415

Val Glu Gln Lys Leu Ile Ser Glu Glu Asp Leu
            420                 425

<210> SEQ ID NO 11
<211> LENGTH: 34
<212> TYPE: DNA
<213> ORGANISM: Artificial Sequence
<220> FEATURE:
<223> OTHER INFORMATION: Synthetic: FRT

<400> SEQUENCE: 11
gaagttccta ttctctagaa agtataggaa cttc                              34

<210> SEQ ID NO 12
<211> LENGTH: 708
<212> TYPE: DNA
<213> ORGANISM: Artificial Sequence
<220> FEATURE:
<223> OTHER INFORMATION: Synthetic: Amino acid sequence of I-SceI
      nuclease

<400> SEQUENCE: 12
atgaagaaca ttaagaagaa ccaggtgatg aacctgggcc ctaactctaa gctgcttaag    60
gaatacaagt ctcagctgat tgagctgaac attgagcagt cgaggctgg cataggcctg    120 attctgggcg atgcttacat taggtctagg gatgagggca agacctactg catgcagttc    180
gagtggaaga acaaggctta catggatcac gtgtgcctgc tgtacgatca gtgggtgctg    240
tctcctcctc acaagaagga gagggtgaac cacttgggaa acctggtgat tacctggggc    300
gctcaaacct tcaagcacca ggctttcaac aagctggctt ctctgttcat tgtgaacaac    360
aagaagacca ttcctaacaa cctggtggag aactacctga ccctatgtc tctggcttac    420 tggttcatgg atgatggcgg caagtgggat tacaacaaga actctaccaa caagtctatt    480
gtgctgaaca cccagtcttt caccttcgag gaggtgaat acctggtgaa gggcctgagg    540
aacaagttcc agctgaactg ctacgtgaag attaacaaga caagcctat tatttacatt    600 gattctatgt cttacctgat tttctacaac ctgattaagc cttacctgat tcctcagatg    660
atgtacaagc tgcctaacac catctcttct gagaccttcc tgaagtga              708

<210> SEQ ID NO 13
<211> LENGTH: 18
<212> TYPE: DNA
<213> ORGANISM: Artificial Sequence
<220> FEATURE:
<223> OTHER INFORMATION: Synthetic: I-SceI recognition site

<400> SEQUENCE: 13
tagggataac agggtaat                                               18

<210> SEQ ID NO 14
<211> LENGTH: 18
<212> TYPE: DNA
<213> ORGANISM: Artificial Sequence
<220> FEATURE:
<223> OTHER INFORMATION: Synthetic: I-SceI recognition site (opposite
      strand)

<400> SEQUENCE: 14
```
attaccctgt tatcccta                                                18

<210> SEQ ID NO 15
<211> LENGTH: 22
<212> TYPE: DNA
<213> ORGANISM: Artificial Sequence
<220> FEATURE:
<223> OTHER INFORMATION: Synthetic: I-CreI recognition site

<400> SEQUENCE: 15
caaaacgtcg tgagacagtt tg                                           22

<210> SEQ ID NO 16
<211> LENGTH: 22
<212> TYPE: DNA
<213> ORGANISM: Artificial Sequence
<220> FEATURE:
<223> OTHER INFORMATION: Synthetic: I-CreI recognition site (opposite
      strand)

<400> SEQUENCE: 16
caaactgtct cacgacgttt tg                                           22

<210> SEQ ID NO 17
<211> LENGTH: 27
<212> TYPE: DNA
<213> ORGANISM: Artificial Sequence
<220> FEATURE:
<223> OTHER INFORMATION: Synthetic: I-CeuI recognition site

<400> SEQUENCE: 17
taactataac ggtcctaagg tagcgaa                                      27

<210> SEQ ID NO 18
<211> LENGTH: 27
<212> TYPE: DNA
<213> ORGANISM: Artificial Sequence
<220> FEATURE:
<223> OTHER INFORMATION: Synthetic: I-CeuI recognition site

<400> SEQUENCE: 18
ttcgctacct taggaccgtt atagtta                                      27

<210> SEQ ID NO 19
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 19
tgcagcccca agcttataac ttcgtatagc atacattata cgaagttatg gatcctaggg   60
ataacag                                                            67

<210> SEQ ID NO 20
<211> LENGTH: 109
<212> TYPE: DNA
<213> ORGANISM: Artificial Sequence
<220> FEATURE:
<223> OTHER INFORMATION: Synthetic oligonucleotide

<400> SEQUENCE: 20
ctggtaccga agttcctatt ctctagaaag tataggaact tcgatcttac cgggcgtata   60
gcatacatta tacgcccggt actgcagccc gacatgtcca atttactga              109

<210> SEQ ID NO 21
<211> LENGTH: 124
<212> TYPE: DNA
<213> ORGANISM: Artificial Sequence
<220> FEATURE:
<223> OTHER INFORMATION: Synthetic: T5-SSI1

<400> SEQUENCE: 21

```
aagcttataa cttcgtatag catacattat acgaagttat ggatcctagg gataacaggg      60
taatattacc ctgttatccc taggatctct agaagctaat tcaagctcta gagatccgtc     120
aaca                                                                  124
```

<210> SEQ ID NO 22
<211> LENGTH: 103
<212> TYPE: DNA
<213> ORGANISM: Artificial Sequence
<220> FEATURE:
<223> OTHER INFORMATION: Synthetic: E1

<400> SEQUENCE: 22

```
aagcttataa cttcgtatag catacattat acgaagttat ggatcctagg gataatccct      60
aggatctcta gaagctaatt caagctctag agatccgtca aca                       103
```

<210> SEQ ID NO 23
<211> LENGTH: 103
<212> TYPE: DNA
<213> ORGANISM: Artificial Sequence
<220> FEATURE:
<223> OTHER INFORMATION: Synthetic: HsE2

<400> SEQUENCE: 23

```
aagcttataa cttcgtatag catacattat acgaagttat ggatcctagg gataatccct      60
aggatctcta gaagctaatt caagctctag agatccgtca aca                       103
```

<210> SEQ ID NO 24
<211> LENGTH: 346
<212> TYPE: DNA
<213> ORGANISM: Artificial Sequence
<220> FEATURE:
<223> OTHER INFORMATION: Synthetic: T5 SSI-2

<400> SEQUENCE: 24

```
ctgcagttca ttcagggcac cggacaggtc ggtcttgaca aaaagaaccg ggcgccctg       60 cgctgacagc cggaacacgg cggcatcaga gcagccgatt gtctgttgtg cccagtcata    120
gccgaatagc ctctccaccc aagcggccgg agaacctgcg tgcaatccat cttgttcaat    180
catgcgaaac gatcctctag gatcgatctg gtaccgaagt tcctattctc tagaaagtat    240
aggaacttcg gatatgtatg ctatacgaag ttataagctt ggggctgcag aagtaacacc    300
aaacaacagg gtgagcatcg acaaaagaaa cagtaccaag caaata                   346
```

<210> SEQ ID NO 25
<211> LENGTH: 114
<212> TYPE: DNA
<213> ORGANISM: Artificial Sequence
<220> FEATURE:
<223> OTHER INFORMATION: Synthetic: B1 SSI

```
<400> SEQUENCE: 25
ggaattcata acttcgtata atgtatgcta tacgcccggt aagatccgaa gttcctatac      60
tttctagaga ataggaactt cggtaccaga tcgatcctag aggatcgttt cgca           114
```

METHOD, VECTORS, CELLS, SEEDS AND KITS FOR STACKING GENES INTO A SINGLE GENOMIC SITE

CROSS-REFERENCE TO RELATED APPLICATIONS

This patent application is a divisional of U.S. 371 patent application Ser. No. 15/114,724 filed Jul. 27, 2016 and issuing as U.S. Pat. No. 10,233,456 on Mar. 19, 2019, which application is a national stage filing under 35 U.S.C. 371 of International Application No. PCT/US2015/013845, filed Jan. 30, 2015, which claims the benefit of priority of U.S. Provisional Patent Application No. 61/933,646, filed Jan. 30, 2014, all of which are incorporated herein by reference in their entirety.

INTRODUCTION

This invention is related to the field of biotechnology, specifically genetic transformation of cells and in particular plants. A method for adding multiple genes into a single genetic locus in cells via sequential transformation is provided herein.

Genetically modified (GM) crops generally express traits that cannot be easily introduced by plant breeding, e.g. herbicide tolerance and insect resistance. Several GM crops expressing single genes for these two traits have been in cultivation since 1996, with their global acreage rapidly increasing in past 16 years. Developing GM plants with multiple genes is considered critical for effective weed and pest management. It is estimated that 8-15 genes will be required for combined weed and pest management in corn. This mandates genetic transformation with multiple genes. Traditional methods are generally impractical for multi-gene transformation because these methods often introduce more than one copy of genes into random sites, leading to silencing of one or more genes. New methods that can precisely add foreign genes into a chosen site can simplify multi-gene transformation and are needed in the art.

SUMMARY

The methods described herein can repeatedly add genes into a chosen locus in a precise manner, which ensures co-segregation of all introduced genes and contributes to the stabilization of gene expression. In addition, methods of removing any additional foreign DNA elements such as selectable markers are provided. A method of gene stacking in cells and particularly in plant cells is provided. The method includes obtaining a seed stock or a cell line comprising a gene stacking site and a vector containing an insert flanked by target sites for a site-specific DNA recombinase both of which are provided herein.

In one aspect, the gene stacking site in the seed stock or cell line is provided and includes a first nuclease recognition site that is upstream from a marker polynucleotide encoding a selectable marker. The selectable marker in the gene stacking site is upstream of a target site for the site-specific recombinase. Alternatively, the gene stacking site may be configured in the opposite orientation such that the target site for the site-specific recombinase is upstream of the marker polynucleotide which is followed by the first nuclease recognition site. The marker polynucleotide lacks a promoter and is encoded such that a promoter placed upstream of the target site for the site-specific recombinase in the gene stacking site can drive expression of the selectable marker. The gene stacking site may optionally include a first promoter operably linked to a first polynucleotide encoding a first polypeptide upstream of the first nuclease recognition site.

In another aspect, a vector including an insert flanked by target sites for a site-specific recombinase oriented in the same direction is provided. The insert includes a marker promoter capable of driving expression of a polynucleotide downstream of one of the target sites for the site-specific recombinase. The marker promoter is followed by a first nuclease recognition site, a second promoter operably connected to a second polynucleotide (gene of interest) encoding a second polypeptide of interest, a second nuclease recognition site and a marker polynucleotide encoding a selectable marker and lacking a promoter. The marker polynucleotide is followed by the second target site for the site-specific DNA recombinase and is encoded such that a promoter placed beyond the second target site for the site-specific recombinase in the vector can drive expression of the selectable marker.

In the gene stacking method provided herein, a first vector based on the vector described above and the site-specific DNA recombinase are introduced into the seed stock or the cell line comprising the gene stacking site described above. The seed stock or cell line is then selected for site-specific integration of the first vector insert by selecting for the selectable marker. Finally, the first nuclease activity is introduced into the seed stock or cell line. The first nuclease is capable of excising the DNA between the two first nuclease recognition sites to remove the marker promoter, one of the target sites for the site-specific DNA recombinase and the marker polynucleotide from the seed stock or cell line. The cellular repair mechanisms or a repair enzyme are allowed to repair the double-stranded break generated by the first nuclease, resulting in the seed stock or cell line being capable of expressing the optional first polypeptide and the second polypeptide, but not the selectable marker.

In another aspect, additional polynucleotides encoding additional polypeptides are introduced into the seed stock or cell line described above at the gene stacking site. The additional polynucleotides may be added by introducing a second vector and the site-specific DNA recombinase into the seed stock or cell line having more than one gene inserted at the gene stacking site. The seed stock or cell line is selected for site-specific integration of the second vector by selecting for the selectable marker. The second nuclease is introduced into the seed stock or cell line and is capable of excising the DNA between the two second nuclease recognition sites to remove the marker promoter, one of the target sites for the site-specific DNA recombinase and one copy of the marker polynucleotide from the seed stock or cell line. The cellular repair mechanisms or repair enzymes are allowed to repair the double-stranded break generated by the second nuclease resulting in the seed stock or cell line being capable of expressing the optional first polypeptide, the second polypeptide and the third polypeptide, but not the selectable marker.

In this aspect, the second vector includes an insert flanked by target sites for the site-specific DNA recombinase. The insert includes a marker promoter capable of driving expression of a polynucleotide downstream of one of the target sites for the site-specific recombinase. The marker promoter is followed by the second nuclease recognition site, a promoter operably connected to a third polynucleotide encoding a third polypeptide, the first nuclease recognition site and the marker polynucleotide encoding the selectable marker and lacking a promoter. The marker polynucleotide is followed by the second target site for the site-specific DNA recombinase.

In still another aspect, kits including a first vector and a second vector are provided. The first vector includes an insert flanked by target sites for a site-specific DNA recombinase in the same orientation to allow recombination and integration into a site containing a similar target site for a site-specific recombinase. The insert includes a marker promoter capable of driving expression of a polynucleotide downstream of one of the target sites for a site-specific recombinase, the promoter followed by a first nuclease recognition site, a multi-cloning site, a second nuclease recognition site and a marker polynucleotide encoding a selectable marker and lacking a promoter. The marker polynucleotide is followed by the second target site for the site-specific DNA recombinase, such that a marker promoter can be positioned downstream of the second target site and drive expression of the selectable marker. The second vector includes an insert flanked by target sites for a site-specific DNA recombinase in the same orientation. The insert comprises a marker promoter capable of driving expression of a polynucleotide downstream of one of the target sites for the site-specific recombinase. The marker promoter is followed by the second nuclease recognition site, a multi-cloning site, the first nuclease recognition site and the marker polynucleotide encoding the selectable marker and lacking a promoter. The marker polynucleotide is followed by the second target site for the site-specific DNA recombinase in the second vector, such that a marker promoter can be positioned downstream of the second target site and drive expression of the selectable marker.

BRIEF DESCRIPTION OF THE DRAWINGS

FIG. 1A shows the gene stacking site (GSS) developed either by random transformation or gene targeting of transgene construct. The construct contains the nuclease I site (magenta bar in middle of construct, ~18 bp), promoterless marker gene (M*), and a loxP site (black triangle, 34 bp). The first gene-of-interest (GOI-1) may be present in this construct. FIG. 1B shows vector 1 used for the first round of transformation. It contains, between two loxP sites, a specific DNA construct consisting of promoter (pro), nuclease I site (I-SceI), GOI-2, nuclease II site (orange bar, I-CreI), and the promoterless marker gene. Co-delivery of Vector 1 with cre gene results in the circularization followed by site-specific integration of the DNA construct. FIG. 1C shows the structure of site-specific integration (SSI) locus, it contains an active marker gene that is now flanked by nuclease I sites. Introduction of nuclease I activity, induces cuts at specific sites (scissors), resulting in the excision of Pro::M cassette, followed by chromosomal repair leading to the formation of the gene stack. FIG. 1D shows the structure of the gene stack after the first round of transformation. In addition to the GOI 1+2, it contains elements for the next round of transformation, i.e. promoterless marker gene (M*) and a single loxP site. Note the presence of nuclease II site for future marker-removal. FIG. 1E shows vector 2 is co-delivered with cre gene in the second round of transformation to add GOI-3. Cre activity catalyzes circularization and integration of Vector 2 construct to form SSI structure, in which marker gene is flanked by nuclease II sites. FIG. 1F shows the introduction of nuclease II activity removes pro::M cassette to stack GOI-3 into the locus (FIG. 1G). As stacking continues, the locus remains open to the next round of transformation (FIG. 1H). By alternating Vector 1 and 2, and nuclease I and II, a number of genes (or set of genes) can be added into the locus. FIG. 1I shows that the M*-loxP fragment can be deleted by nuclease and Cre activity to develop a marker-free 'clean' stack (final stack) prior to the release of transgenic plant.

FIGS. 6A-6D show a schematic representation of the molecular strategy for gene stacking into the T5 site as described in the Examples. FIG. 6A shows a schematic of the T5 site containing a Cre gene expressed by a strong promoter, Ubi, with lox76 site placed between the promoter and the start codon of the Cre gene. Hyg-R is the hygromycin selection gene (35S:HPT:nosT). FIG. 6B is a schematic showing pNS27, constructed to initiate gene stacking at T5 site, which contains a fragment of genes between loxP and lox75. This fragment consists of promoterless (*) Bar gene flanked by I-SceI sites, a functional GFP gene, and a promoterless (*) NPT gene inversely orientated, with FRT at its 5' end and CCR5 sequence (ZFN recognition site) at its 3' end. FIG. 6C is a schematic showing the expected structure after particle bombardment of pNS27 into T5 cells resulting in the formation of site-specific integration (SSI) structure that is selected on bialaphos due to activation of the Bar gene. Cre-mediated lox75×lox76 recombination between pNS27 and the T5 site generates loxP and lox78 at the SSI site as shown. Since lox78 is double mutant site, it is mostly incapable to further recombine. The SSI site also contains promoterless NPT gene fused to FRT at 5' end and CCR5 sequence at 3' end to facilitate next round of gene stacking. FIG. 6D is a schematic showing introduction of I-SceI activity in SSI cells results in the excision of Bar gene leaving a loxP and FRT for next round of gene stacking.

FIGS. 7A-7F are a set of figures showing the site specific gene integration at the T5 site. FIG. 7A is a schematic of the T5-SSI structure. EcoRI (E) sites in the locus, and primers sites across the two lox sites, and the fragment sizes (kb) are indicated. FIG. 7B is a photograph of a gel showing the PCR amplicons generated from the T5-SSI lines using primers across loxP and lox78 junctions in the SSI structure. The 2.5 kb and 1.4 kb amplicons indicated the presence of the expected SSI structure. FIGS. 7C and 7D show the DNA sequence of the amplicons which confirmed the origin of SSI structure from Cre-lox recombination. FIG. 7E is a photograph of a representative Southern analysis of EcoRI-digested genomic DNA of SSI lines showing the presence of the expected bands with GFP and nosT probes. nosT is present in each gene generating 3 distinct bands. FIG. 7F is a photograph showing GFP expression in the callus of SSI lines.

FIGS. 8A-8E are a set of figures showing I-SceI-induced marker gene excision from T5-site-specific integration (T5-SSI) site. FIGS. 8A and 8B are schematics of the structure of T5-SSI locus before (FIG. 8A) and after (FIG. 8B) the excision of Bar gene. Primers located in Ubi and GFP sequences amplify a 1.9 kb fragment from the unexcised site, and a 0.8 kb from the correctly excised site. FIG. 8C is a photograph of a PCR analysis showing excision of Bar gene induced by transient expression of the strong I-SceI (Ubi:ISceI) gene. Representative PCR analysis on excision (E) lines with Ubi-GFP primers showing 0.8 kb or 'no amplification', indicating near-perfect Bar excision or the presence of large indels. Some lines failed to excise Bar gene as indicated by the amplification of the parental 1.9 kb band. FIG. 8D is a photograph of a PCR analysis showing excision of Bar gene by heat-inducible I-SceI gene. Three samples of HsE1 and HsE2 were analyzed by PCR to detect Bar excision. Amplification of 0.8 kb band in HsE2 indicated near-perfect excision in HsE2 line. T5-SSI and the non-transformed (NT) wild-type lines serve as positive and negative controls. FIG. 8E shows representative DNA sequence of 0.8 kb amplicon indicating near-perfect excision of Bar gene through cut and ligation process. loxP, I-SceI and GFP sequences are indicated. Dashed line represent missing sequence and joining of the two cut ends (red-blue highlighted parts).

FIGS. 9A-9E are a set of figures showing southern analysis of the marker gene excision (E) lines derived from transformation of T5-SSI lines with Ubi:ISceI gene. FIGS. 9A and 9B are schematics showing the SSI structure before (FIG. 9A) and after (FIG. 9B) Bar gene excision. KpnI (K) sites and fragments sizes are shown. FIG. 9C-9E photographs of the southern blots showing hybridization of KpnI-digested genomic blot with GFP, Bar and I-SceI probes, respectively, indicating excision of Bar gene, and absence of a functional copy of I-SceI gene. Red arrows point to the perfectly excised excision (E) lines as indicated by the presence of 3.6 kb band.

FIGS. 10A-10F are a set of figures showing site-specific integration of GUS gene at T5 site. FIG. 10A is a schematic showing the structure of marker-free SSI site derived from the GFP gene integration and Bar excision from T5 site (see FIG. 6A-6D). FIG. 10B is a schematic of plasmid pNS35 which was constructed for site-specific gene integration at the FRT located at T5 site. It contains FRT flanked fragment consisting of inversely placed Ubi promoter, CCR5-ZFN recognition site, GUS reporter gene, I-SceI site, and inversely oriented promoterless (*) NPT gene. FIG. 10C is a schematic showing the SSI product after co-bombardment of pNS35 with FLPe gene into marker-free SSI cells results in the formation of a selectable (geneticin) SSI structure, in which, GUS gene is stacked with GFP at the T5 site. The fusion of Ubi promoter with NPT gene forms a unique junction within the SSI structure and FIG. 10D displays representative PCR analysis of SSI lines showing the amplification of the expected 1.5 kb unique junction in some lines (indicated by blue arrows), a shorter amplicon or no amplification in others, indicating imperfect site-specific integration. FIG. 10E provides the DNA sequencing of the 1.5 kb amplicon to reveal the perfect sequence consisting of NPT gene (red font), FRT (shaded), and Ubi promoter (yellow). The underlined sequences are the expected restriction sites. FIG. 10F shows a schematic depiction of the SSI 'junction' structure.

FIGS. 11A-11D show a schematic representation of the molecular strategy for gene stacking into the B1 site as described in the Examples. FIG. 11A is a schematic showing the B1 site contains a constitutively expressed GUS reporter gene (Ubi:GUS) flanked by oppositely oriented loxP sites. Due to opposite orientation of loxP sites, the Ubi:GUS gene fragment could invert in the presence of Cre activity. B1 site contains T-DNA right and left borders (RB, LB) on either ends of the construct. FIG. 11B is a schematic of pNS29, which was constructed for initiating gene stacking at B1 site. The construct is flanked by lox75 and loxP sites, and geneticin selection marker (35S:NPT) between I-SceI recognition sites. It also contains gene stacking site consisting of FRT site fused to promoterless NPT gene followed by CCR5 site. GFP gene serves as the gene-of-interest. FIG. 11C is a schematic showing the gene structure after co-bombardment of pNS29 with Cre expression construct (pUbi:Cre) may generate site-specific integration structures via loxP×loxP recombination. It should be noted that integration of pNS29 construct could occur at either or both loxP sites at B1 locus (only one of shown). The GFP and GUS genes are stacked in the SSI locus. FIG. 11D is a schematic showing that the introduction of I-SceI activity excises 35S:NPT fragment from the locus generating a marker-free stack of GUS and GFP gene leaving the gene stacking site (FRT:NPT:CCR5).

FIGS. 12A-12G are a set of figures showing site-specific integration at the B1 site. FIGS. 12A and 12B are schematics of the two possible SSI structures originating from Cre-lox mediated site-specific integration of pNS29 construct at B1 site. Primers sites and the expected amplicon sizes are shown in the bottom. EcoRI (E), KpnI (K), and EcoRV (EV) sites in the locus, and the fragment sizes (kb) are indicated in FIG. 12A. FIGS. 12C and 12D are photographs of representative PCR analysis of SSI lines using GUS-NPT and Ubi-NPT primers to distinguish SSI structures. PCR was also done to detect the presence or absence of Cre gene, which is expected to be absent. FIG. 12E is a photograph of Southern analysis of E, K or EV-digested genomic DNA of SSI-5 line showing the presence of the expected bands with GFP probe. SSI-3 and SSI-4 were found to contain complex integrations, and therefore, removed from further analysis. FIG. 12F shows the DNA sequence of the 0.8 kb amplicon from SSI-5 and confirms the presence of a perfect SSI structure. FIG. 12G is a photograph showing GFP expression in the callus of SSI-5 line.

FIGS. 13A-13C are a set of figures showing schematics and PCR analysis of excision (E) lines derived from transformation of B1-SSI lines with Ubi:ISceI gene. FIGS. 13A and 13B are schematics of the SSI structure before (FIG. 13A) and after (FIG. 13B) I-SceI-mediated 35S:NPT gene excision. PCR primer sites used to detect the presence or absence of 35S:NPT gene are shown in FIG. 13A. FIG. 13C is a photograph of PCR analysis showing the presence of 35S:NPT gene in the parental SSI line and absence in one of the excision line.

DETAILED DESCRIPTION

Figure 1:
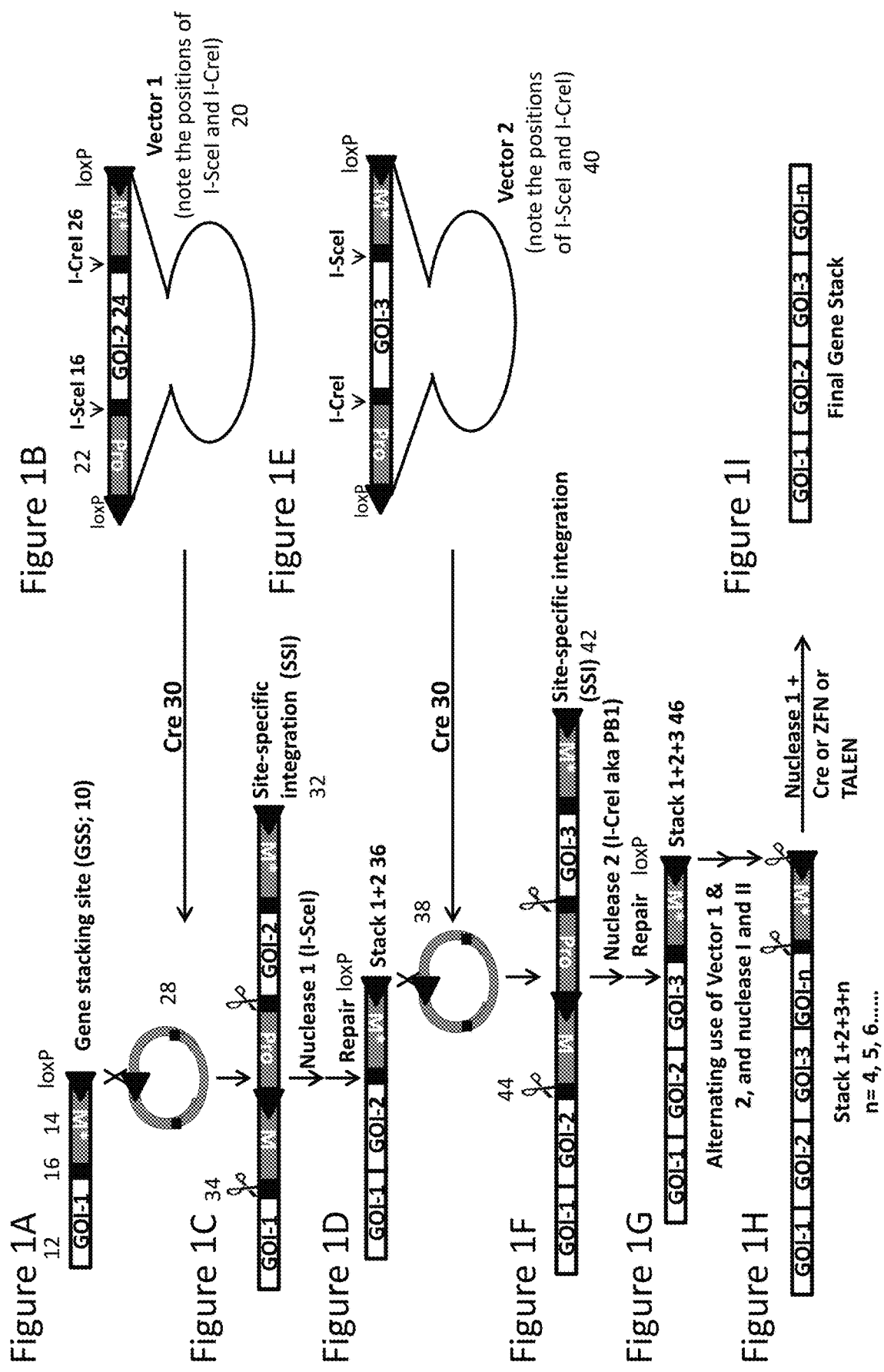
FIGS. 1A-1I show a simplified schematic depiction of the molecular strategy for gene stacking through an iterative plant transformation process as provided herein.

A method is described herein for repeatedly directing the integration of individual genes (or a set of genes) into cellular genomes, such as plant genomes. The sites of integration may be characterized and known as sites for integration of foreign genes that have no adverse effects on the cells. Many of these integration sites are characterized in various cells and those of skill in the art are capable of choosing an appropriate site for integration. Transgenic cells or plants developed by this method would contain a stack (or an array) of genes in a single genomic site without the presence of selectable marker genes. Linking genes in this manner will simplify breeding of transgenic crops as the "stack" will essentially behave as a single gene during reproduction. In addition, precise integration of genes into the characterized site will minimize gene expression variation caused by complex integrations or inopportune integration into 'unfavorable' sites, such as within heterochromatin or essential genes. Plant transformation processes generally rely on the use of a selectable marker gene (SMG), and repeated transformation necessitates its recycling. Therefore, removal of the SMG in each round of transformation is incorporated in the method. Further, since plant transformation is generally an inefficient and complex process, a robust and precise mechanism is employed for the gene-integration step.

The combination of the two steps, gene-integration and SMG-removal, and use of the proposed DNA constructs, enables unlimited rounds of transformation. The resulting transgenic plants will contain only genes-of-interest (without SMG), enhancing the quality of the clones, and making this method suitable for intragenic technologies. Intragenic technology comprises genetic engineering of plants with genes originating from the same species or related species without incorporating DNA from bacteria, virus or animal genomes. This method could be used either for introducing a large fragment of DNA containing multiple genes or adding single genes or a set of genes one by one into the selected site.

The method described herein utilizes two molecular tools: (a) a robust efficient site-specific recombination system such as the Cre-loxP or Flp-FRT system for integration of the gene of interest, and (b) a pair of nucleases, such as I-SceI and I-CreI, for the excision of the selectable marker gene. The nucleases should have rather large or complex recognition sites such that the sites are infrequent in the genome and likely to be destroyed upon re-ligation. Precise and efficient integration of genes into the selected genomic site (a gene stacking site 10) is guided by the site-specific recombinase system, in which the clones containing site-specific integrations are selected by a gene-trapping approach. Two examples of efficient SSR systems are Cre-lox or FLPe-FRT that display high efficiency and undetectable toxicity in the tested plant genomes.

The resulting transgenic clones are subjected to nuclease reaction by the first nuclease such as I-SceI. There are a number of nucleases that function at high efficiency in plant cells, e.g., I-SceI and CCR5 ZFN. Nuclease activity excises out the selectable marker gene (SMG) as well as the second target site for site-specific recombination, leaving behind a single target site for the second round of transformation consisting of gene integration by the site-specific recombinase and SMG excision by the second nuclease such as I-CreI. Through multiple rounds of transformations, involving site-specific recombinase mediated gene integration, and alternating use of a first nuclease and a second nuclease for SMG excisions, an unlimited number of genes can be stacked into a single locus in a cell line, such as a plant cell line. See FIG. 1A-1I. This approach is transferrable to the transgenic crop plant upon targeted insertion of the gene stacking site. Regardless, the method would suitably be practiced on founder lines that contain a dedicated gene stacking (GS) site 10.

The components used in the method are also provided herein and kits for carrying out the method are also described. As described herein the efficiency of each step in the process is high, and therefore the gene stacking method will provide an efficient means of introducing multiple genes into a cell to produce a tissue or organism. The first component of the method is a site-specific recombinase and the target sites for the site-specific recombinase. For example, the P1 phage derived Cre-loxP recombination system. In this system, Cre (SEQ ID NO: 2) is the recombinase protein and loxP is the recombination target site. The loxP site is a 34 bp sequence (5'-ATAACTTCGTATAG-CATACATTATACGAAGTTAT-3'; SEQ ID NO: 3). Several loxP variants have been identified and can initiate Cre mediated recombination. The loxP variants include lox75 (5'-taccgggCGTATA GCATACAT TATACGAAGTTAT-3'; SEQ ID NO: 4), lox76 (5'-ATAACTTCGTATA GCATACAT TATACGcccggta-3'; SEQ ID NO: 5) and lox78 (5'-taccgggCGTATA GCATACAT TATACGcccggta-3' SEQ ID NO: 6). Other variants are available to those of skill in the art and may be used herein. Plant genomes have not been found to contain the loxP sequence, so a loxP site is first added to the genome by standard plant transformation. Cell lines containing a single loxP site are used for Cre-mediated gene integration. In the Examples a cell line with two inverse loxP sites was used. This method has been demonstrated in many cell types and plants species including tobacco, *Arabidopsis*, and rice (Albert et al., 1995; Vergunst et al, 1998; Srivastava et al., 2002), and works at efficiencies similar to that of the standard transformation methods. For example, rice transformation efficiency by particle bombardment is ~50%, and Cre-mediated transformation efficiency in rice ranges from 30-60%. In addition to confirming the position of gene insertion, use of Cre-lox system introduces precision in the integration process as Cre-lox recombination does not involve addition or deletion of even a single nucleotide. This precision is important in the stability of the transgene as demonstrated by Srivastava et al. (2004), Chawla et al. (2006), Nanto et al. (2009), and Akbudak et al. (2010). In summary, Cre-lox mediated site-specific integration has been demonstrated to be highly efficient in both dicotyledonous and monocotyledonous plants. Further, transgene integration structures developed by Cre-lox recombination are predictable, precise, and stable.

While Cre-lox recombination is the most widely used site-specific recombination system, other systems are known and may be used instead of or interchangeably with the Cre-lox recombination system such as the Flp-FRT recombination system, Dre-rox recombination system, PhiC31-attP/attB or another of the phage integrases. The Flp-FRT system was also used in the Examples and shown to be effective in rice. The Flp recombinase (SEQ ID NO: 8 and 10) mediates recombination between two FRT sites (5'-GAAGTTCCTATTC TCTAGAAA GTATAGGAACTTC-3'; SEQ ID NO: 11). Those of skill in the art will appreciate that there are several ways to obtain expression of the site specific recombinase in cells. The site specific recombinase may be integrated into the cell at the gene stacking site and expressed from an inducible or constitutive promoter. Alternatively, the recombinase can be expressed from a distal site within the cell from an inducible or constitutive promoter. In another embodiment, the site specific recombinase can be expressed from an expression vector that is transformed into the cell with the vector containing the gene of interest as described herein. The site specific recombinase may be expressed from a separate vector or the same vector carrying the gene of interest. In yet another embodiment, the site specific recombinase may be delivered to the cell via a protein mediated delivery system. Methods for transforming cells with nucleic acids and methods of protein mediated delivery are available to those of skill in the art but include particle bombardment, *Agrobacterium*-mediated transformation, protoplast, transduction, or liposome or nanoparticle mediated delivery systems.

Nuclease-induced chromosomal breaks and their repair by the cellular or enzymatic processes is the second major component of the system described herein. Nucleases introduce double-stranded breaks (DSB) or single-stranded breaks in DNA. If a DSB occurs in the chromosome, it is repaired efficiently by a cellular repair mechanism called non-homologous end joining (NHEJ). During this process some DNA sequences near the breakpoint are generally deleted, and the broken ends are ligated (Puchta, 2005). Therefore, repaired sites often contain short deletions (1-20 bp) at the breakpoint, especially if the DSB is induced by a strong nuclease activity (Petolino et al., 2010; Lloyd et al., 2012; Weinthal et al., 2013). Endonucleases such as I-SceI, I-Cre-I, I-CeuI or designer nucleases such as zinc-finger nuclease (ZFN), transcription-activator-like effector nucleases (TALEN) or clustered regularly interspaced short palindromic repeats systems (CRISPR/Cas9) have been used in cells, including plant cells to delete transgenes with efficiencies reaching up to 34% (Petolino et al., 2010; Weinthal et al., 2013). The I-SceI nuclease recognizes an 18 bp site and leaves a four base overhang shown by the arrows in the recognition site below:

```
                (SEQ ID NO: 13 and 14, respectively)
5' . . . T A G G G A T A A↓C A G G

G T A A T . . . 3'

3' . . . A T C C C↑T A T T G T C C

C A T T A . . . 5'.
```

The I-CreI nuclease recognizes a 22 bp site and leaves a four base overhang shown by the arrows in the recognition site below:

```
                (SEQ ID NO: 15 and 16, respectively)
5' . . . CAAAACGTC GTGA↓GACAGTTTG . . . 3'

3' . . . GTTTTGCAG↑CACT CTGTCAAAC . . . 5'.
```

The I-CeuI nuclease recognizes a 27 bp site and leaves a four base overhang shown by the arrows in the recognition site below:

```
                (SEQ ID NO: 17 and 18, respectively)
5' . . . TAACTATAACGGTCCTAA↓GGTAGCGAA . . . 3'

3' . . . ATTGATATTGCCAG↑GATTCCATCGCTT . . . 5'.
```

Other rare cutting endonucleases are available to those of skill in the art including but not limited to I-MsoI, I-DmoI, I-SceII-VII, I-ChuI and many others.

The molecular strategy underlying the gene stacking method is depicted in FIG. 1A-1I. The first step in the method is generation of a genomic site for gene stacking 10 either by random integration of the DNA construct shown in FIG. 1A or by homologous recombination mediated gene targeting of the same construct (enabled by ZFNs, TALENs or CRISPR). The design of this DNA construct (shown in FIG. 1A) and its integration into a cell line or seed stock is provided herein. In addition to an optional gene-of-interest (GOI-1; 12), it contains DNA fragments designed for gene stacking—a promoterless selectable marker gene (M*; 14) in an inverted orientation and flanked by a first nuclease recognition site (e.g. I-SceI; 16) on the left side, and a loxP site or other target site for site-specific recombination on the right side (18). The selectable marker polynucleotide (14) is positioned such that a promoter inserted after recombination at the target site (18) will drive expression of the selectable marker (14) and allow for selection of the cells for recombinants. Once integrated as a single full-length copy in the genome, this site serves as the "gene stacking site" (GSS; 10) within a cell line or seed stock.

The next step in the method is construction of a first transformation vector as shown in FIG. 1B. The vector contains a DNA construct between two target sites for a site-specific recombinase such as loxP sites 18. The construct inserted between the two target sites contains a strong promoter (Pro; 22) for driving expression of the integrated marker gene followed by a first nuclease recognition site 16, the GOI operably connected to a promoter (GOI-2; 24), a second nuclease recognition site (26; e.g. I-CreI), and the promoterless marker gene 14. The promoterless marker gene 14 should be located and oriented such that a promoter placed outside the target site 18 will drive expression of the marker gene across the target site. The marker gene in the vector can be the same marker gene included in the GSS 10 or a different marker gene. The first and second nucleases and nuclease recognition sites on the other hand must be distinct from each other. Co-delivery of the first vector 20 with a recombinase gene 30 in an expression construct after inducing expression of an integrated recombinase or with the recombinase protein such as Cre, using methods such as particle bombardment and *Agrobacterium* results in the separation of the DNA construct from the vector backbone via target site recombination within the first vector 20. The construct circle (the insert; 28) could then integrate into the GSS 10 via site-specific recombinase-mediated recombination resulting in site-specific integration of the construct insert (SSI; 32, FIG. 1C). In the SSI structure, the marker promoter/selectable marker polynucleotide (pro::M) fusion 22, 14 facilitates selection via expression of the selectable marker 14, which is flanked by the first nuclease recognition sites 16. Transient site-specific recombinase activity is likely to be used in this process, and the selected SSI clones are unlikely to contain the site-specific recombinase gene if an expression construct is used because stable recombinase activity may destabilize the SSI structure.

Next the first nuclease activity 34 is introduced into the SSI lines to initiate the excision and repair reaction. Nuclease activity can be introduced into the cells by either (i) re-transformation of cells with an expression vector comprising the first nuclease gene; (ii) inducing nuclease expression, e.g. by chemical or heat treatment, via an inducible first nuclease gene placed in or found in the GSS-containing cells; or (iii) crossing SSI plants with plants expressing the first nuclease gene. The first nuclease activity induces double-stranded breaks (DSB) at the nuclease recognition sites around the pro::M cassette, resulting in its excision. The chromosomal DSBs are repaired by cellular repair mechanisms called non-homologous end joining (NHEJ), leading to the joining of the broken ends and deletion of the first nuclease recognition sites. As a result, a stack of GOI 1+2 will be developed with elements necessary for the next round of site-specific integration (M*; 14 and loxP; 18) and future marker excision (second nuclease recognition sites 26; FIG. 1D).

For the next round of gene stacking, a second transformation vector (40; FIG. 1E) is used. It is similar to the first transformation vector 20, but the positions of the first nuclease recognition site 16 (e.g. I-SceI) and the second nuclease recognition site 26 (e.g. I-CreI) have been swapped, relative to the positions in the first transformation vector 20. This arrangement is necessary for iterative transformation process. Co-delivery of the second transformation vector 40 with the site-specific recombinase 30 will generate the 'construct circle' 38 as described above, followed by integration into the target site 18 for the site-specific recombinase located in stack 1+2 (the GSS), forming a SSI structure 42 (FIG. 1F). Next, the second nuclease activity 44 is introduced to remove pro::M cassette, and generate a stack of GOI 1+2+3 (46; FIG. 1G).

If a final gene stack has been developed, the M*-target site (loxP) fragment can be potentially removed by introducing the second nuclease and site-specific recombinase activities. The nuclease will generate a DSB at the specific recognition site and site-specific recombinase will generate single stranded nicks at the target sites for the site-specific recombinase. The repair of DSB and nicks could lead to the removal of M*-target site fragment from the SSI structure, resulting in a 'clean' stack of genes that does not include any foreign elements if the GOIs and the promoters used in the gene stack are native to the cell or the cell type. In some cases the site-specific recombinase-induced nicks are not repaired efficiently, and target site-specific TALEN, ZFN or CRISPR system can be used instead. TALEN and ZFN induce DSB, which will be repaired via NHEJ.

Alternatively, additional genes can be stacked into the gene stacking site, using additional rounds of transformation. The third round of transformation can be done using the first vector 20 with a novel gene of interest as compared to that used in the first round of transformation and the site-specific recombinase 30 followed by marker-excision by the first nuclease 16. Thus, by alternating the first vector 20 and the second vector 40, and the first nuclease (16; I-SceI) and the second nuclease (26; I-CreI), respectively in rounds of transformation and excision allows for multi-gene stacking. Using alternative rounds of transformation and excision provides for an unlimited number of genes to be placed into the specific genomic site.

This method provides several advantages to current methods. First, the method provides for simplified breeding processes when multiple genes are carried in a single genome at a single site and on a single chromosome. The number of F2 plants required for breeding multi-genic traits exponentially increases with the increase in locus number (4^n, where n=number of loci). Therefore, methods for developing 'molecular stacks' encoding important traits are important for simplifying breeding of transgenic crops.

The method allows expression of multi-gene traits such as metabolic pathways in a transgenic cell or organism. Metabolic pathways generally involve coordinated expression of multiple genes. Gene stacking approaches are more suitable for engineering metabolic pathways as undesired mis-regulation of genes due to 'position effect' is minimized.

The precision of the transformation and integration of the genes of interest is useful to ensure stable expression. Introduction of a single-copy of the DNA construct containing genes is important for ensuring stable gene expression. Increased copy number of introduced genes has been shown to correlate with lower expression. The position of the integration in the genome may also influence the expression of introduced genes, sometimes adversely. Recombinase mediated gene integration obviates these problems by directing integration of a single copy of DNA into a selected site.

Site-specific recombinases offer increased efficiency of transformation and integration into the genome. For overall efficiency of the process, it is critical to use efficient molecular tools. By using site-specific recombination systems such as Cre-lox and Flp-FRT, the gene-integration process remains as efficient as in the traditional methods. In other words, use of a site-specific recombinase system such as Cre-lox and Flp-FRT does not compromise the efficiency of the process, while adding precision to it.

The selectable marker 14 can be reused in subsequent rounds of selection and removed from the cell once the process is completed. Selectable markers are important tools of plant transformation process; however, their presence in transgenic crops is undesirable. Moreover the available selectable markers are limited in number. Therefore, it is better to remove them after the transformed clones have been isolated. In this method, marker-removal is accomplished in such a way that the site is concomitantly prepared for the next round of transformation. Further, the same selectable marker 14 can be used in each round, and therefore transformation efficiency, which is highly reliant on the selectable marker chosen, does not vary between rounds of transformation. Selectable markers genes for use in the methods described herein include but are not limited to genes capable of mediating positive and negative selection and include antibiotic resistance genes, genes capable of making plants resistant to herbicides or environmental toxins or resistance to disease. Selectable markers include those conveying neomycin resistance, bleomycin resistance, kanamycin resistance, spectinomycin resistance, streptomycin resistance, glyphosphate resistance, and hygromycin resistance, and enzymes including chloramphenicol acetyltransferase, dehalogenase, D amino acid oxidase, as well as others available to those of skill in the art.

Figure 2:
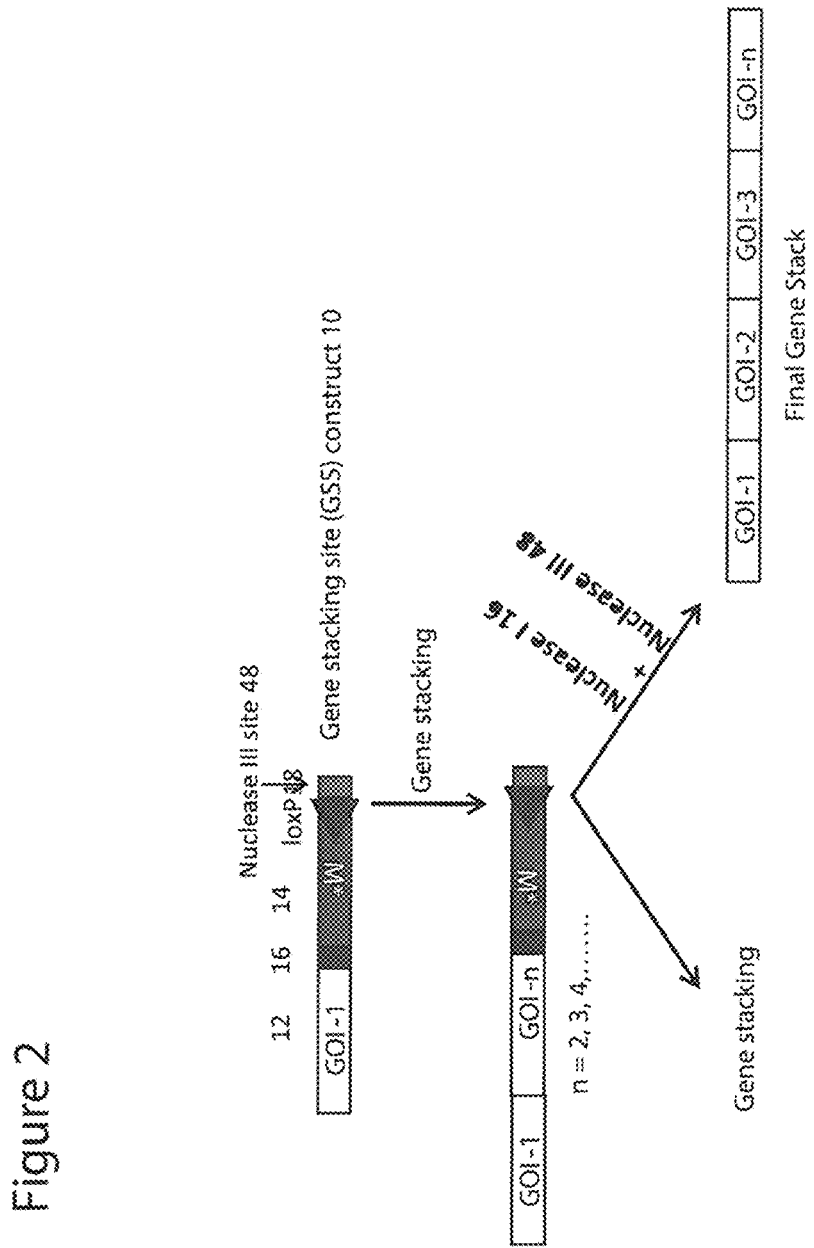
FIG. 2 is a schematic depiction of a modified gene stacking site to allow for removal of the marker gene and target site for the site-specific recombinase. In addition to the elements described in FIG. 1A, a modified GSS construct contains a nuclease III site (yellow bar labeled nuclease III). Transformation with Vector 1 and 2 (see FIGS. 1B and 1E) into the modified GSS will generate a gene stack in which promoterless marker gene and loxP sites are flanked by nuclease I and III sites. Introduction of nuclease I and III activities will generate the 'final gene stack' without the presence of marker gene, loxP site or nuclease sites, which are undesirable elements in a transgene locus.

In one embodiment, the gene stacking site 10 may contain a third nuclease recognition site 48 on the opposite side of the target site 18 for the site-specific recombinase from the marker polynucleotide encoding the selectable marker 14. See FIG. 2. This third nuclease recognition site 48 can be used after the final round of transformation and excision in combination with the nuclease specific for the nuclease recognition site following the marker gene 14 as shown in FIG. 2 to remove the final copy of the marker gene 14 left after the final round of gene stacking.

Figure 3:
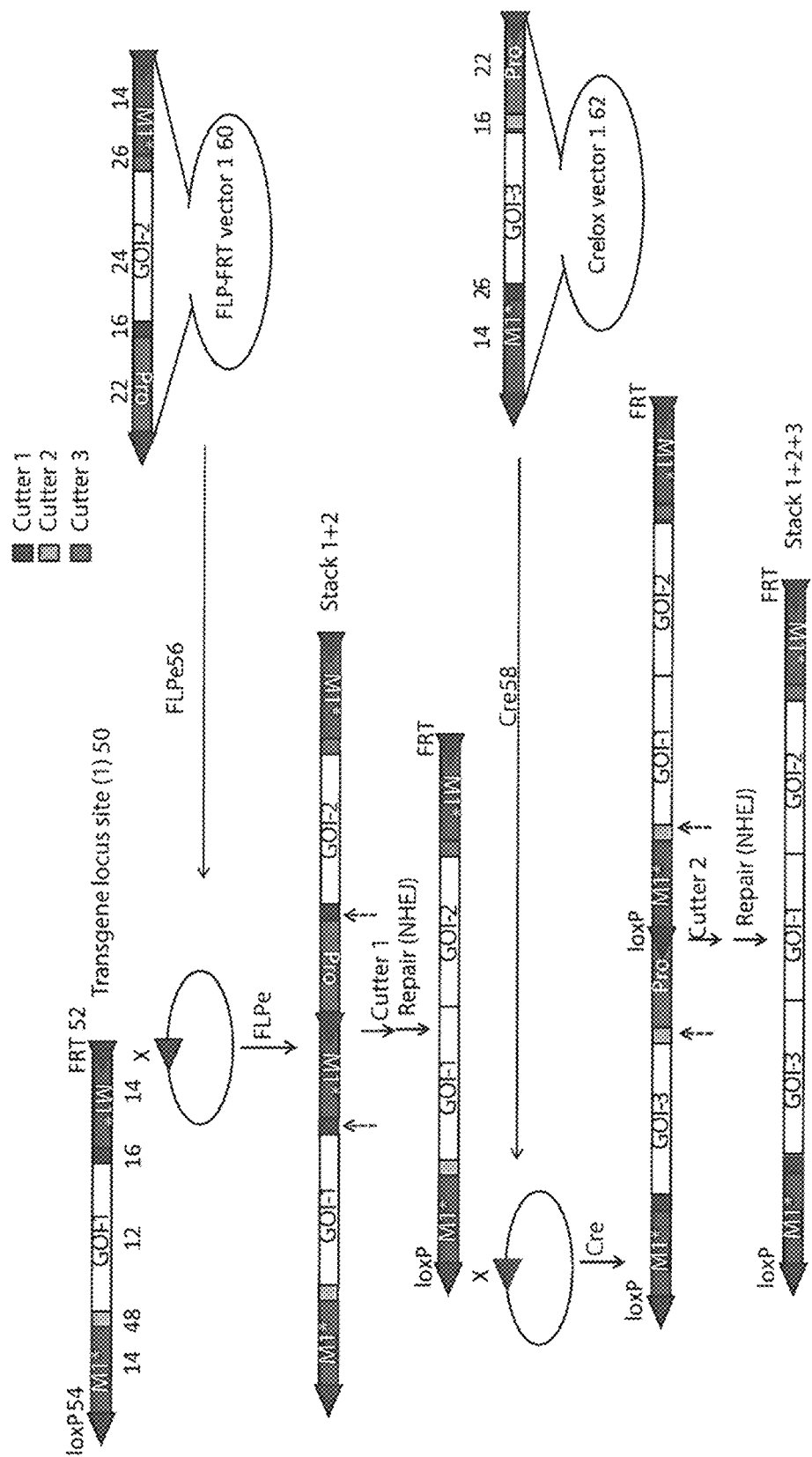
FIG. 3 is an alternative schematic depiction of the gene stacking process provided herein in which two site-specific recombinases are used alternatively to generate the stack of genes for expression in the cell.
Figure 3:
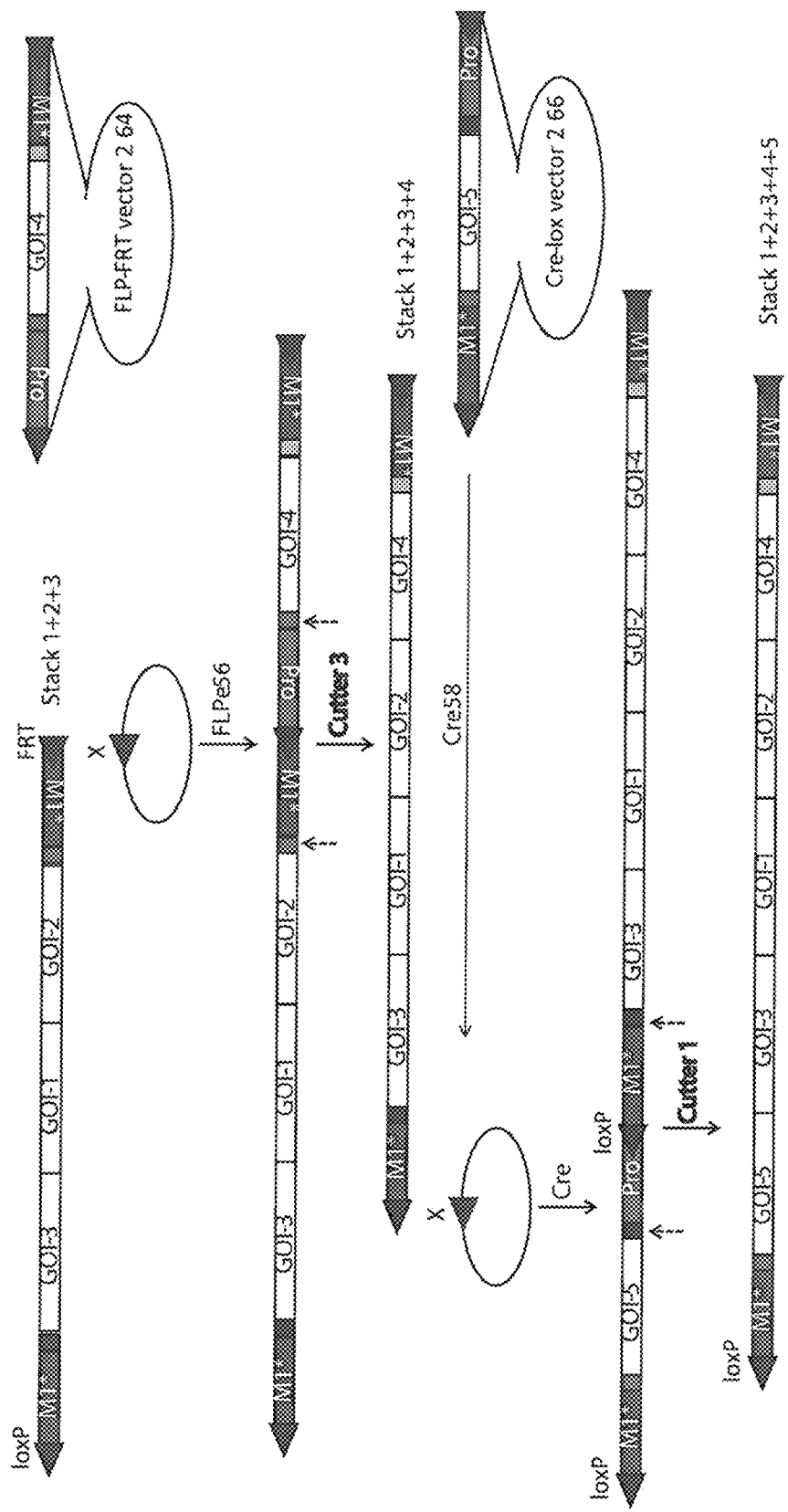
Figure 3:
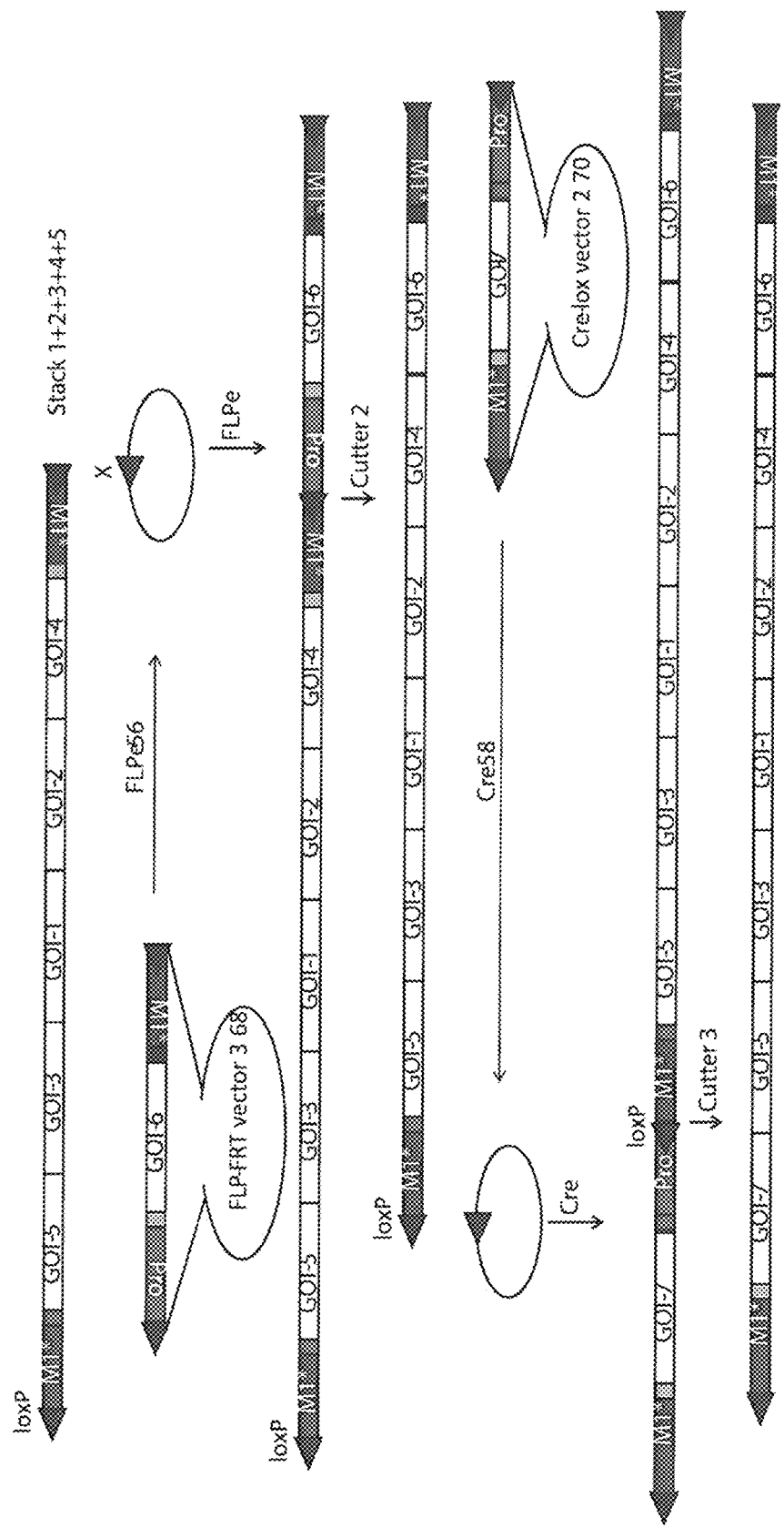

FIG. 3 provides an alternative gene stacking strategy in which two site-specific recombinases are used in the method. The gene stacking site 10 is flanked by one target site 52 for the first site-specific recombinase 56 and by a second target site 54 for the second site-specific recombinase 58. The first vector 60 in which the insert is flanked by target sites 52 for the first site-specific recombinase 56 and the GOI-2 24 is recombined into the GSS 10 by transforming cells comprising the GSS 10 with the first site-specific recombinase 56. After excision with the first nuclease and repair, the cell comprising the GSS now including GOI1 and GOI2 is transformed with the second site-specific recombinase 58 and a second vector 62 in which the insert is flanked by target sites 54 for the second site-specific recombinase 58, the nuclease recognition sites 16, 48 are changed as compared to the first vector and the GOI3 is within the insert. The marker 14 is selected to select for the SSI. The insert of the second vector 62 is recombined into the GSS 10 and excision with the second nuclease results in removal of the selectable marker. The process can be continued alternating the target sites and positions of the nuclease recognitions sites in the vector used and using the site-specific recombinases alternatively to stack as many genes in the single integration site as one may desire as shown in FIG. 3 parts 2 and 3.

Figure 4:
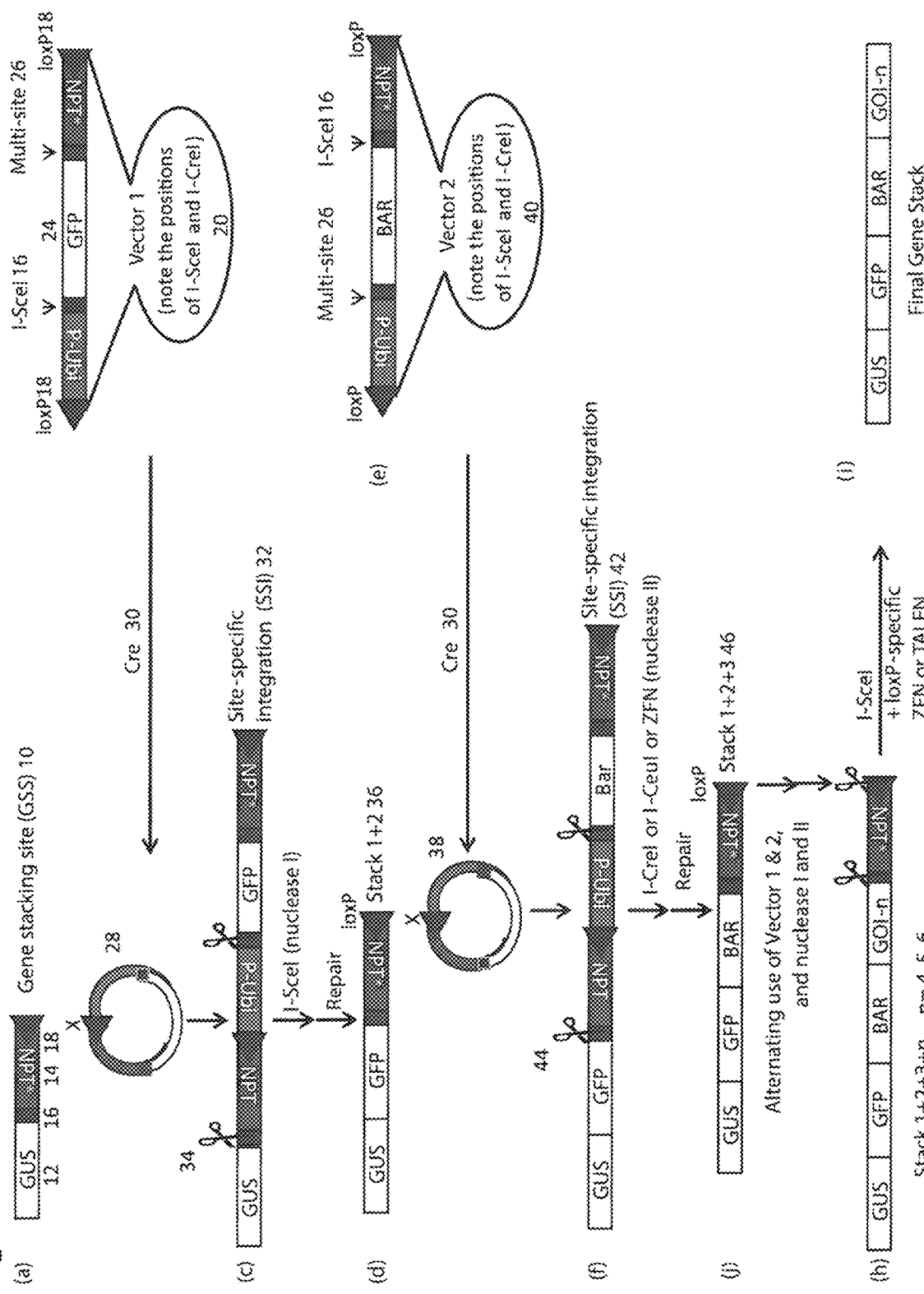
FIG. 4 is a schematic depiction of the gene stacking method described in the examples.

FIG. 4 provides a constructive model of the methods described herein. In the method a single marker protein 14 the neomycin phosphotransferase gene without any promoter (NPT*) is used to introduce three polynucleotides into the genome stacking site 10. In the method the multi-site refers to a site containing more than a single nuclease recognition site 26, such that more than one nuclease may be used or a nuclease which results in destruction of the nuclease site may be used, but a second nuclease will remain able to recognize the site. In FIG. 4, a 75 base pair site comprising recognition sites for I-CeuI, I-CreI and ZFN CCR5 is included. See Perez et al., 2008. The gene stacking site 10 has a β-glucuronidase gene driven by maize ubiquitin promoter 12, a I-SceI recognition site as the first nuclease recognition site 16 and a loxP site as the target site for the recombinase 18. The first vector 20 has an insert flanked by loxP sites 18 with an insert containing the maize ubiquitin-1 promoter 22 positioned to direct expression of the promoterless marker 14 after integration of the insert into the gene stacking site 10. The first nuclease recognition site 16 is followed by a second gene of interest 24 which is green fluorescent protein driven by the 35S promoter in FIG. 4 and flanked by the second nuclease recognition site 26 which is a multi-enzyme recognition site and the promoterless marker gene (*NPT; 14). The Cre recombinase 30 is used to generate the site specific integration intermediate (SSI) and the first nuclease is used to remove the marker gene after selection for the SSI. The second vector 40 has an insert flanked by loxP sites and the insert includes the nuclease recognition sites in the reverse orientation as compared to the first vector. The third gene of interest in this example is the BAR gene encoding phosphothricin acetyl transferase driven by the rice actin-1 promoter. This example demonstrates that a wide variety of genes of interest and promoters capable of driving expression of these genes may be used in the methods described herein.

The GSS or final cells comprising the stack of genes may also include a reporter gene capable of being used to select transgenic cells. The reporter polypeptide may be selected from a fluorescent polypeptide such as GFP, a luciferase, a β-glucoronidase, a chloramphenicol acetyltransferase or any other reporter polypeptide available to those of skill in the art.

The gene stacking method and vectors described herein may be used in a wide variety of cell types, but is especially suited to development of transgenic plants that can be generated to carry a number of genes without a selectable marker and allowing for passage of the genes to the next generation of plants without requiring further genetic manipulation and even using traditional breeding. Plants for use in the methods described herein include, but are not limited to *Arabidopsis*, tobacco, rice, wheat, oat, soybean, corn, cotton, papaya, sugar beet, alfalfa, squash, potato, tomato or canola (rapeseed). Promoters for use in the methods will depend on the species and possible tissue origin of cells being used in the methods. Many inducible and constitutive promoters are known to those of skill in the art and the precise selection will depend on factors related to the application. Inducible promoters include, but are not limited to those that can be controlled by external stimuli such as chemical, heat, cold or light. Some of the examples are: (a) Chemical/β-estradiol inducible XVE promoter; (b) Heat-shock *Arabidopsis* HSP81-1; (c) Cold-inducible *Arabidopsis* cor15 promoter; (d) Heat-shock HSP17.5E soybean promoter. Constitutive promoters include but are not limited to (a) Maize ubiquitin-1 promoter; (b) Cauliflower mosaic virus 35S promoter; (c) Rice actin-1 promoter; (d) Rice ubiquitin-1 promoter.

Kits for performing the methods described herein are also provided. The kits include a first vector and a second vector. The first vector includes an insert flanked by target sites for a site-specific DNA recombinase. The target sites are present in the vector in the same orientation relative to each other to allow recombination and integration into a site containing a similar target site for a site-specific recombinase. The insert includes a marker promoter capable of driving expression of a polynucleotide downstream of one of the target sites for a site-specific recombinase. The promoter is followed by a first nuclease recognition site, a multi-cloning site, a second nuclease recognition site and a marker polynucleotide encoding a selectable marker and lacking a promoter. The marker polynucleotide is followed by the second target site for the site-specific DNA recombinase, such that a marker promoter can be positioned downstream of the second target site and drive expression of the selectable marker. The second vector includes an insert flanked by target sites for a site-specific DNA recombinase in the same orientation relative to each other. The insert comprises a marker promoter capable of driving expression of a polynucleotide downstream of one of the target sites for the site-specific recombinase. The marker promoter is followed by the second nuclease recognition site, a multi-cloning site, the first nuclease recognition site and the marker polynucleotide encoding the selectable marker and lacking a promoter. The marker polynucleotide is followed by the second target site for the site-specific DNA recombinase in the second vector, such that a marker promoter can be positioned downstream of the second target site and drive expression of the selectable marker. The main distinction between the two vectors is that the two nuclease sites are reversed as compared to the other vector.

The kit may also include other components necessary to carry out the methods described herein. The kit may include a cell, callus or seed stock comprising a gene stacking site. The gene stacking site includes a first nuclease recognition site upstream from a marker polynucleotide encoding a selectable marker which is upstream of the at least one target site for a site specific DNA recombinase. The gene stacking site may also include a promoter operably linked to a first polynucleotide encoding a first polypeptide upstream of the first nuclease recognition site. This first polypeptide may include a reported polypeptide. The marker polynucleotide encoding the selectable marker is oriented such that a promoter inserted on the downstream side of the target site for recombination can be inserted in a recombination event at the target site and will drive expression of the selectable marker.

The kit may also include a vector for generating a cell line or seed stock with a gene stacking site. The insert of such a vector may include a multi-cloning site for insertion of a polynucleotide encoding a gene of interest, the first nuclease recognition site, a third marker polynucleotide encoding a third selectable marker and a target site for a site-specific recombinase. The insert in this vector may be flanked by restriction endonuclease recognition sites for more than one restriction endonuclease. The kits may also include proteins for protein mediated delivery to cells or vectors allowing for expression of the site-specific recombinase and/or multiple nucleases for use in the methods described herein. The vectors described herein are suitably plasmids, such as expression vectors but may also be any other suitable vector for carrying, transmitting and/or replicating DNA of interest, including viral vectors, BACs, YACs or other means.

The Examples provide a proof-of-concept (POC) for the insertion of multiple genes into specified genomic sites through cycles of gene insertions and marker gene excisions. The method was demonstrated on the model crop, rice, by stacking GFP gene into the specified genomic sites, called T5 and B1. Leveraging the superior recombination efficiency of the site-specific recombination system, Cre-lox, we obtained gene integration into the lox site at ~50% efficiency. The site-specific integration was selected by a promoter-trap strategy, involving the insertion of promoter-less marker gene downstream of the promoter located at the genomic site. The resulting site-specific integration structure contained a precise single-copy insertion of the gene fragment flanked by two recombination sites. The marker gene along with one of the two recombination sites was excised by the endonuclease, I-SceI, leaving the GFP gene and the FRT site for the next round of site-specific integration. The endonuclease mediated DNA excision in which only a short insertion-deletions occurred (the desirable outcome as opposed to large insertion-deletions) was observed at ~25% efficiency. We then inserted GUS gene into the FRT site at ~30% efficiency. In the resulting site-specific integration structure, GFP and GUS gene were linked and the selection marker gene, NPT, was flanked by ZFN sites to facilitate marker-excision and preparation of the site for the next round of gene stacking. In conclusion, we have developed a method by which genes can be inserted repeatedly into the specified genomic site for developing a stack of the genes-of-interest.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Examples

Figure 5:
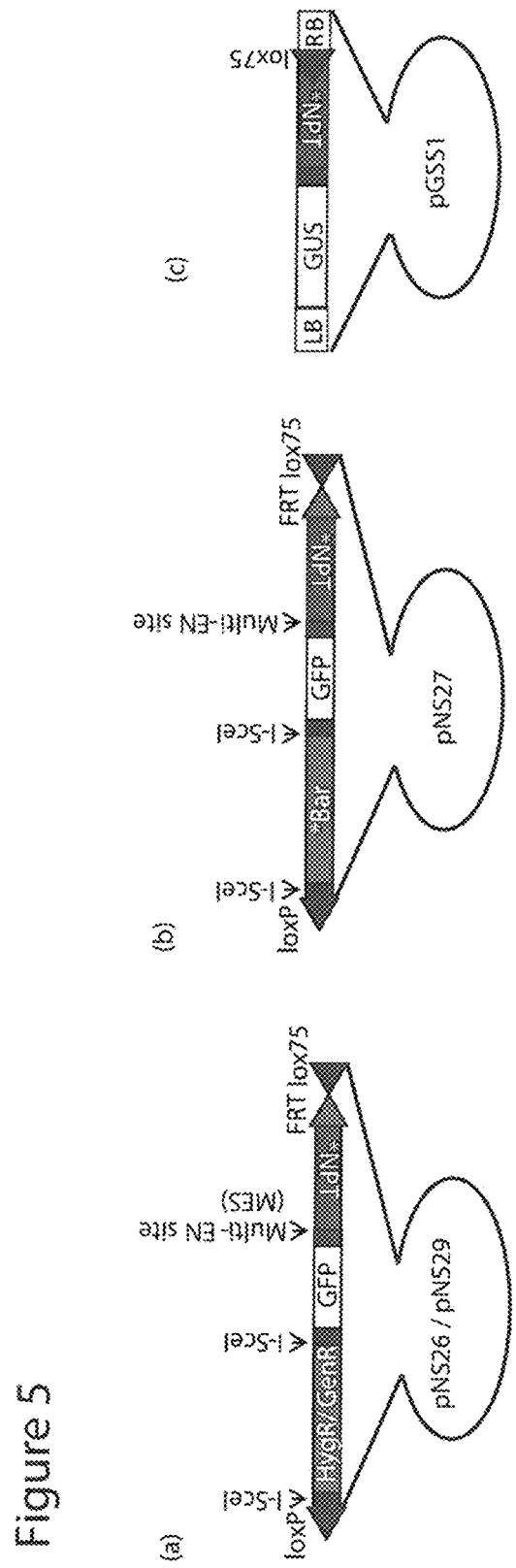
FIG. 5 is a schematic depiction of the DNA vectors constructed in the Examples for use in the methods.

Material and Methods:
DNA Vectors:
Four DNA vectors, pNS26, pNS27, pNS29, and pGSS1 were developed. The pNS series are gene stacking vectors for site-specific integration into target lox sites, and the pGSS1 is a target site vector to develop lox target sites in rice genome. pNS26 and pNS29 allow site-specific integration of a fully operable selection marker gene: hygromycin resistance gene [HygR (35S:HPT:nos3')] in pNS26 and geniticin resistance gene [GenR (35S:NPT:nos3')] in pNS29 [FIG. 5(a)]. These marker genes are flanked by I-SceI recognition sites followed by fully a operable GFP gene (synthetic Green Fluorescent Protein) as a gene-of-interest, a multi-endonuclease site (MES) and a promoter-less neomycin phosphotransferase gene (*NPT). The MES contains recognition sequences for three endonucleases: I-CreI, I-CeuI, and CCR5 ZFN to allow marker removal during gene stacking by anyone of these endonucleases. Next to *NPT, an FRT site is located for allowing site-specific integration by Flp-FRT system. The whole construction is flanked by loxP site and lox75 as shown in FIG. 5(a). Lox75 is variant of loxP that contains mutations in the left inverted repeat sequence (Albert et al., 1995).

pNS27 contains the same features as pNS26 except that HygR gene was replaced with a promoter-less Bar gene (*Bar) that encodes bialaphos resistance [FIG. 5(b)]. The final DNA vector, pGSS1, was made in a binary T-DNA vector (pPZP200) and contains between LB and RB (T-DNA borders), a fully operable GUS gene followed by a I-SceI recognition sequence, a promoter-less NPT (*NPT) and lox75 sequence [FIG. 5(c)]. pGSS1 was transferred to *Agrobacterium tumefaciens* EHA105 for rice transformation.

Cell Lines (Seed Stocks):
The method described above is being developed on rice cell lines, B1 and T5, which were already available in the lab. GSS1 line is under development.

B1 Lines:
B1 line (rice cultivar Nipponbare) contains a marker-free site-specific integration of a chimeric GUS gene (betaglucuronidase gene driven by maize ubiquitin-1 promoter) flanked by oppositely oriented loxP sites [FIG. 6(a)]. This orientation of loxP sites does not permit excision of GUS gene by Cre-lox recombination, but can invert the GUS gene in forward or reverse orientation. LoxP sites in B1 line serve as gene stacking sites.

T5 Line:

T5 (rice cultivar Taipei-309) is also a previously developed lox-target line that contains a variant lox site, lox76, between the promoter (maize ubiquitin-1) and cre coding sequence. Lox76 contains 8-bp mutations in its right inverted repeat (Albert et al., 1995). Thus, T5 site is suitable for gene trapping approach for selecting site-specific integration and expresses Cre. Also present in the site is a hygromycin resistance gene (HygR) that is designated as the first gene-of-interest [FIG. 6B].

Transformation of Cell Lines:

Rice tissue culture was done according to protocol of Nishimura et al. (2006). Seeds of homozygous B1 and T5 genotypes were plated on callus induction media. B1 callus was used for transformation with pNS29, and T5 for transformation with pNS27. B1 was co-transformed with pNS29 and pUbiCre. pUbiCre provides Cre activity in B1 cells. DNA was coated on 1 micron gold particles (1.5 mg) using the standard CaCl2/spermidine protocol. For T5 transformation, pNS27 (5 µg) was used without pUbiCre. The final DNA-coated particles were suspended in 100 µl absolute ethanol for particle bombardment by PDS1000/He gene gun (Bio-Rad, Inc.). The bombarded callus was selected on appropriate chemical [geneticin (100 mg/l) or Bialaphos' (5 mg/l)]. It took 4-6 weeks to visually identify transgenic clones.

Characterization of Clones:

Transgenic clones were visually evaluated for GFP expression using BlueStar flash light (Nightsea Inc.). Small portion of growing callus was collected for DNA isolation and polymerase chain reaction (PCR) to characterize integration locus.

Results:

Development of GSS Lines:

Three GSS lines were developed using *Agrobacterium*-mediated transformation of rice (cv. Nipponbare) with pGSS1. These lines express GUS gene, their molecular analysis is pending. In the meantime, proof-of-concept study was initiated with B1 and T5 lines.

Molecular Strategy of Gene Stacking into T5 Line:

FIG. 6A-6D show the molecular strategy of gene stacking into the T5 line. The strategy for stacking into the T5 site involves delivery of pNS27 into T5 cells, where it will separate from its backbone and generate a gene circle (FIG. 6B. The insertion of gene circle into lox76 site generates a site-specific integration (SSI) structure [FIG. 6C], in which the Bar gene traps the cre-promoter making it selectable on bialaphos. This structure is now suitable for gene stacking as it contains (i) I-SceI site on either ends of Bar gene to recycle it, (ii) promoter-less NPT gene for gene trapping, and (iii) FRT site for site-specific integration by Flp-FRT recombination [FIG. 6C]. The Ubi:Bar gene (herbicide resistance) could be left in the site as a second gene of interest or removed by I-SceI action to generate a new structure shown in FIG. 6D. Please note removal of the Bar gene is not necessary for gene stacking as NPT gene will be used for next round of selection. While the gene stacking structure in T5 locus is not perfect (it contains a disrupted Ubi:cre gene), it allows testing the proposed strategy, and therefore, is suitable for proof-of-concept study.

Molecular Analysis of T5-SSI Lines:

The T5-SSI lines were isolated on the bialaphos containing media. We obtained 5 bialaphos-resistant lines (SSI1-5) that were subjected to PCR analysis to verify the presence of SSI structure (see FIG. 7A). These 5 lines were obtained from the 10 bombarded plates (50% efficiency). PCR using primers located on the two unique junctions in the SSI structure, Ubi-loxP-Bar and NPT-FRT-lox78-Cre, are expected to amplify 2.5 kb and 1.4 kb fragments, respectively. Using the genomic DNA of each SSI line, the predicted 2.5 kb fragment was amplified from all 5 lines, but the 1.4 kb fragment was amplified from 4 out of 5 lines (SSI-1, 3, 4, 5) (see FIG. 7B). The amplified fragments were sequenced to obtain the top strand and the bottom strand sequences. Each sequence perfectly matched the predicted SSI junction sequences, and contained loxP or FRT-lox78 sequences (FIGS. 7C and 7D), indicating the origin of SSI structure from Cre-lox recombination (lox75×lox76=loxP and lox78). Each line was also subjected to Southern analysis to evaluate the overall SSI structure. EcoRI-digested genomic DNA was blotted and probed with the $P^{32}$-labeled GFP and nosT fragments. GFP hybridization is expected to generate 3.7 kb band, and nosT hybridization would generate two additional bands, 1.6 kb and 1.5 kb, if only a single insertion is present. The nosT fragment is located at the 3' end of each gene (not shown in FIG. 7A). The four SSI lines, SSI-1, 3, 4, 5, showed the predicted bands on the Southern blots confirming the presence of a single SSI insertion at the T5 site (FIG. 7E). Each line also expressed GFP gene indicated by green fluorescence under blue light (FIG. 7F). The control cell line appears pale yellow under blue light (not shown).

I-SceI-Mediated Marker Excision from T5-SSI Lines:

Three T5-SSI lines, 1, 3, and 5, were retransformed with pUbi:ISceI or pHSP:ISceI, which yielded 57 Ubi:ISceI lines (Excision or 'E' lines), and 11 HSP:ISceI lines (Heat-shock Excision or 'HsE' lines). Presence of the functional I-SceI gene in these E lines was, however, not detected, indicating toxicity of the strong I-SceI expression in rice cells. PCR on E lines using primers across the Bar gene yielded a 1.9 kb amplicon from the parental T5-SSI lines (FIG. 8A), whereas, 0.8 kb amplicon is expected if I-SceI induced DSB-repair leads to a near-perfect excision (FIG. 8B). Thirty-six E lines (63%) failed to amplify the parental 1.9 kb band indicating excision of the Bar gene. Seventeen of these lines (29%) generated a strong 0.8 kb band, indicating near-perfect excision, the remaining either did not generate any amplicon or generated shorter amplicons, indicating the presence of large deletions at the excision site (see FIG. 8C). The sequencing of 0.8 kb band from different E lines verified the presence of the perfect excision footprint indicating a cut and ligation reaction at the site (FIG. 8E). Two HsE lines were heat-treated at 42° C. for 3 hours, allowed to recover for 72 h, and subjected to PCR. Three samples of each line were analyzed by PCR that generated 0.8 kb amplicon from HsE-2 samples (FIG. 8D), which also consisted of the perfect cut-ligation footprint (FIG. 8E). Heat-shock I-SceI gene, as expected, also amplified the parental 1.9 kb band, indicating the presence of the mosaic excision events in the tissue (FIG. 8D).

Next, E lines were analyzed by Southern hybridization of the genomic DNA digested by KpnI (FIGS. 9A-9E). T5-SSI locus is expected to contain three KpnI (K) sites, and generate a 2 kb GFP fragment (FIG. 9A). The near-perfect excision of Bar gene (~1 kb) would generate~3.6 kb fragment instead (FIG. 9B). Southern hybridization showed 2 kb GFP band on KpnI digested T5-SSI genomic DNA, and variable fragments on the E lines, including the 3.6 kb band (FIG. 9C). As expected, all E lines lacked Bar gene (FIG. 9D), confirming its excision from the genome. Hybridization with I-SceI gene indicated the presence of I-SceI fragments in the genome of E lines; however, since I-SceI could not be amplified using PCR from these lines, truncated copies of I-SceI gene were possibly detected on the Southern blot (FIG. 9E).

Site-Specific Integration of GUS Gene at the T5 Site:

Using E1 and E4 as the founder lines for the next round of gene stacking, GUS gene was inserted into the FRT site at the T5 locus (FIGS. 10A-10F). E1 and E4 contain an FRT site fused to the promoterless NPT gene for gene stacking (FIG. 10A). A donor vector, pNS35, was constructed for this purpose, which contained FRT-flanked DNA fragment consisting of maize ubiquitin promoter (ZmUbi1) (oriented to activate the promoterless NPT gene), heat-inducible GUS gene (HSP:GUS), and a promoterless NPT gene (for the next round of gene stacking) (FIG. 10B). Using the gene gun method, pNS35 was co-bombarded with pUbiFLPe into E1 or E4 cell cultures. The bombarded cells were selected on geneticin containing media to isolate site-specific integration events resulting from FRT×FRT recombination. In the predicted site-specific integration (SSI) structure, Ubi promoter is placed in front of the NPT gene to confer geneticin resistance. From three experiments, 24 geneticin resistant lines were recovered, 11 of which have been analyzed by PCR. The SSI structure contains a single unique junction, NPT:FRT:Ubi. The second predicted junction, NPT:FRT:lox78:Cre, is identical to that present in the parental E1, E4 site (see FIG. 10A, 10C). Using PCR, the unique NPT:FRT:Ubi junction was amplified from 7 out of 11 lines (FIG. 10D); however, only 4 contained the expected 1.5 kb amplicon, while the remaining contained a shorter than expected junction. DNA sequencing of these fragments indicated the perfect sequence in the 1.5 kb amplicons (FIG. 10E). As expected, NPT sequence was fused to the Ubi promoter sequence through FRT×FRT recombination (FIG. 10F). Thus, we have demonstrated the ability to stack at least two genes at a single site and the resultant clones may be used for further gene stacking using these methods.

Molecular Strategy of Gene Stacking into B1 Line:

FIGS. 11A-11D show the molecular strategy of gene stacking into the B1 site. B1 locus contains a marker-free GUS gene flanked by loxP sites (FIG. 11A). The donor vector, pNS29, contains a functional selection marker gene, 35S:NPT, to select the transformants. The 35S:NPT gene is flanked by I-SceI sites to facilitate its excision (FIG. 11B). pNS29 also contains GFP gene and a marker-free NPT gene for the next round of gene stacking. pNS29 was co-bombarded with the Cre expression vector (pUbi:Cre) for site-specific integration of pNS29 construct into one of the two loxP at B1 site (FIG. 11C). It should be noted that site-specific insertion of pNS29 construct is not selectable. Therefore, we screened~40 transgenic lines by PCR for isolating the B1-SSI lines. Three lines were found to contain site-specific integration into one of the two lox sites at the B1 site (FIGS. 12A-12G). The remaining lines possibly contained random insertions of pNS29, and were therefore discarded.

This gene stacking locus is expected to contain (i) a promoter-less NPT gene (*NPT) for the next round of gene stacking by promoter trapping approach, (ii) FRT site for Flp-mediated gene integration, and (iii) the CCR5 ZFN site (FIG. 11D). Site-specific integration into FRT site of the next gene (e.g. Bar gene) followed by marker-removal by CCR5 ZFN enzymes would allow gene stacking of the third gene into the locus, and so on.

Molecular Analysis of B1-SSI Lines:

The B1 founder line contains two loxP sites on either ends of the Ubi:GUS gene (FIG. 11A). Therefore, site-specific integration of the pNS29 construct into the loxP sites is not selectable. When B1 cells were co-bombarded with pNS29 and pUbi:Cre, a number of geneticin-resistant lines were obtained owing to the presence of 35S:NPT gene in pNS29. These B1-transformants were screened by PCR to discern SSI from random insertions. Cre-lox mediated SSI into one of the two loxP sites in B1 locus would generate two distinct SSI structures, consisting of either GUS-lox75-FRT-NPT or NPT-FRT-lox75-Ubi junctions (FIGS. 12A and 12B). PCR using primers, designed to detect these junctions, identified 3 putative SSI lines among~40 B1-transformants (FIGS. 12C and 12D) One line, SSI-5, contained GUS-lox75-FRT-NPT (FIG. 12A), and two SSI-3, 4 contained NPT-FRT-lox75-Ubi junction (FIG. 12B). For the SSI structures to be stable, sustained expression (integration) of the co-bombarded Cre gene is not tolerated. PCR using cre primers confirmed the absence of Cre gene from these lines (FIGS. 12C and 12D). Southern analysis of these lines showed the presence of single-copy insertion in SSI-5 (FIG. 12E), and multi-copy insertions in SSI-3, 4. Genomic DNA of SSI-5 was digested with KpnI, EcoRV or EcoRI and hybridized with a GFP probe. In a single insertion event, >6.8 kb, 3.9 kb, and >4.3 kb bands are expected (see FIG. 12A). Line SSI-5 fit this criteria and was therefore called a single-copy SSI line (FIG. 12E). Therefore, SSI-5 was selected for the follow up work. The 0.8 kb PCR band from SSI-5 was sequenced, and found to contain the expected lox75-FRT sequence originating from Cre-lox mediated site-specific integration of pNS29 construct (FIG. 12F). Line SSI-5 strongly expressed GFP gene (FIG. 12G).

I-SceI-Mediated Marker Excision from B1-SSI Line:

The B1-SSI line was retransformed with Ubi:ISceI gene to induce excision of the 35S:NPT gene (see FIGS. 13A and 13B). About 10 lines were obtained, two of which have been analyzed to date. PCR was done to amplify 35S:NPT gene, which was present in one of the excision lines but absent in the other, indicating the excision of I-SceI flanked 35S:NPT fragment (FIG. 13C). Southern analysis and sequencing to confirm precise excision are ongoing.

REFERENCES

Akbubak et al. (2010) Dosage-dependent gene expression from direct repeat locus in rice developed by site specific gene integration. *Mol Biotechnol.* 45:15-23.

Albert et al. (1995) Site-specific integration of DNA into wild-type and mutant lox sites placed in the plant genome. *Plant J.* 7:649-59.

Antunes et al. (2012) Targeted DNA excision in *Arabidopsis* by a re-engineered homing endonuclease. *BMC Biotechnol.* 12: 86.

Chawla et al. (2006) Transgene expression produced by biolistic-mediated, site-specific gene integration is consistently inherited by the subsequent generations. *Plant Biotech J.* 4: 209-218.

Dietz-Pfeilstetter (2010) Stability of transgene expression as a challenge for genetic engineering. *Plant Science* 179: 164-7.

Halpin (2005) Gene stacking in transgenic plants—the challenge for 21st century plant biotechnology. *Plant Biotech. J.* 3:141-55.

James (2012) Global Status of Commercialized Biotech/GM Crops: 2012. ISAAA Brief No. 44. ISAAA: Ithaca, N.Y.

Lloyd et al. (2012) Single molecule PCR reveals similar patterns of non-homologous DSB repair in tobacco and *Arabidopsis*. *PLoS One* 7(2):e32255.

Nanto et al. (2009) Expression of a transgene exchanged by the recombinase-mediated cassette exchange (RMCE) method in plants. *Plant Cell Rep.* 28:777-85.

Nishimura A, Aichi I, and Matsuoka M (2006) A protocol for *Agrobacterium*-mediated transformation in rice. *Nat. Protocol.* 1, 2796-2802.

Perez et al. (2008) Establishment of HIV-1 resistance in CD4+ T cells by genome editing using zinc-finger nucleases. *Nat Biotechnol.* 26, 808-816.

Petolino et al. (2010) Zinc finger nuclease-mediated transgene deletion. *Plant Mol. Biol.* 73:617-628.

Puchta (2005) The repair of double-strand breaks in plants: mechanisms and consequences for genome evolution. *J. Exp. Bot.* 56: 1-14.

Que et al. (2010) Trait stacking in transgenic crops: Challenges and opportunities. *GM Crops* 1:4, 220-229.

Srivastava et al. (2004) Cre-mediated site-specific gene integration for consistent gene expression. *Plant Biotech. J.* 2: 169-179.

Srivastava and Ow (2001) Site-specific gene integration in rice. *Mol. Breed.* 8: 345-350.

Vergunst et al. (1998) Site-specific integration of *Agrobacterium* T-DNA in *Arabidopsis thaliana* mediated by Cre recombinase. *Nucleic Acids Res.* 26:2729-34.

Weinthal et al. (2013) Non-homologous end-joining-mediated gene replacement in plant cells. Plant Physiol. 162: 390-400.

We claim:

1. A vector comprising an insert flanked by target sites for a site-specific DNA recombinase, wherein the target sites are in the same orientation, the insert comprising a first-promoter capable of driving expression of a downstream polynucleotide, a first nuclease recognition site upstream of the first promoter, a multi-cloning site between the first nuclease recognition site and a second nuclease recognition site that is different from the first nuclease recognition site, and a marker polynucleotide encoding a selectable marker and lacking a promoter, the marker polynucleotide flanked by the second target site for the site-specific DNA recombinase, such that a second promoter can be positioned on the opposite side of the second target site to drive expression of the selectable marker, wherein the nuclease recognition sites are recognition sites for a non-recombinase nuclease.

2. The vector of claim 1, wherein the target sites for the site-specific DNA recombinase are selected from the group consisting of loxP sites, FRT sites, and rox sites.

3. The vector of claim 1, wherein the nuclease recognition sites are selected to be recognition sites for a nuclease selected from the group consisting of I-SceI, I-CreI, I-CeuI, I-MsoI, I-DmoI, I-SceII-VII, I-ChuI, TALEN, and ZFN, or a site targetable by CRISPR/Cas-9 guide RNA.

4. The vector of claim 1, wherein the selectable marker is selected from the group consisting of markers encoding neomycin resistance, bleomycin resistance, kanamycin resistance, spectinomycin resistance, geniticin resistance, streptomycin resistance, chloramphenicol acetyltransferase, dehalogenase, D amino acid oxidase, glyphosphate resistance, and hygromycin resistance.

\* \* \* \* \*